(12) United States Patent
Lemperle et al.

(10) Patent No.: US 6,432,045 B2
(45) Date of Patent: Aug. 13, 2002

(54) URETHRA SURGICAL DEVICE

(75) Inventors: Stefan M. Lemperle, La Jolla; Corbett Stone, San Diego; Brian Kelleher, Ramona, all of CA (US); David Lipsitz, Charlotte, NC (US)

(73) Assignee: Artes Medical, La Jolla, CA (US)

(*) Notice: Subject to any disclaimer, the term of this patent is extended or adjusted under 35 U.S.C. 154(b) by 0 days.

(21) Appl. No.: 09/825,484

(22) Filed: Apr. 2, 2001

Related U.S. Application Data

(60) Provisional application No. 60/242,945, filed on Oct. 24, 2000, provisional application No. 60/198,698, filed on Apr. 20, 2000, and provisional application No. 60/193,666, filed on Mar. 31, 2000.

(51) Int. Cl.[7] ............................................. A61B 1/307
(52) U.S. Cl. ...................... 600/135; 600/210; 600/220; 600/200; 604/517
(58) Field of Search .............................. 600/200, 210, 600/211, 212, 220, 135; 604/517

(56) References Cited

U.S. PATENT DOCUMENTS

| | | | | |
|---|---|---|---|---|
| 2,292,237 A | * | 8/1942 | Parcher | 128/9 |
| 3,110,304 A | * | 11/1963 | Hartman | 128/9 |
| 4,785,796 A | * | 11/1988 | Mattson | 128/9 |
| 5,688,224 A | * | 11/1997 | Forkey et al. | 600/200 |
| 5,928,138 A | * | 7/1999 | Knight et al. | 600/201 |
| 6,165,125 A | * | 12/2000 | Elliott | 600/200 |

* cited by examiner

*Primary Examiner*—Linda C. M. Dvorak
*Assistant Examiner*—Jocelyn Ram
(74) *Attorney, Agent, or Firm*—Stout, Uxa, Buyan & Mullins, LLP

(57) ABSTRACT

A surgical device for expanding and viewing tissue is disclosed. The surgical device includes a handle, an insertion probe, and at least one window disposed within the insertion probe. The handle has a proximal end and a distal end, and the handle is sized and shaped to be held by a surgeon. The insertion probe has a proximal end, a distal end, and a longitudinal axis extending between the proximal end and the distal end. The proximal end of the insertion probe is removably attached to the distal end of the handle. The window extends along a length of the longitudinal axis, and has an opening that is sufficient in size to allow tissue to prolapse through the window and into the insertion probe.

27 Claims, 19 Drawing Sheets

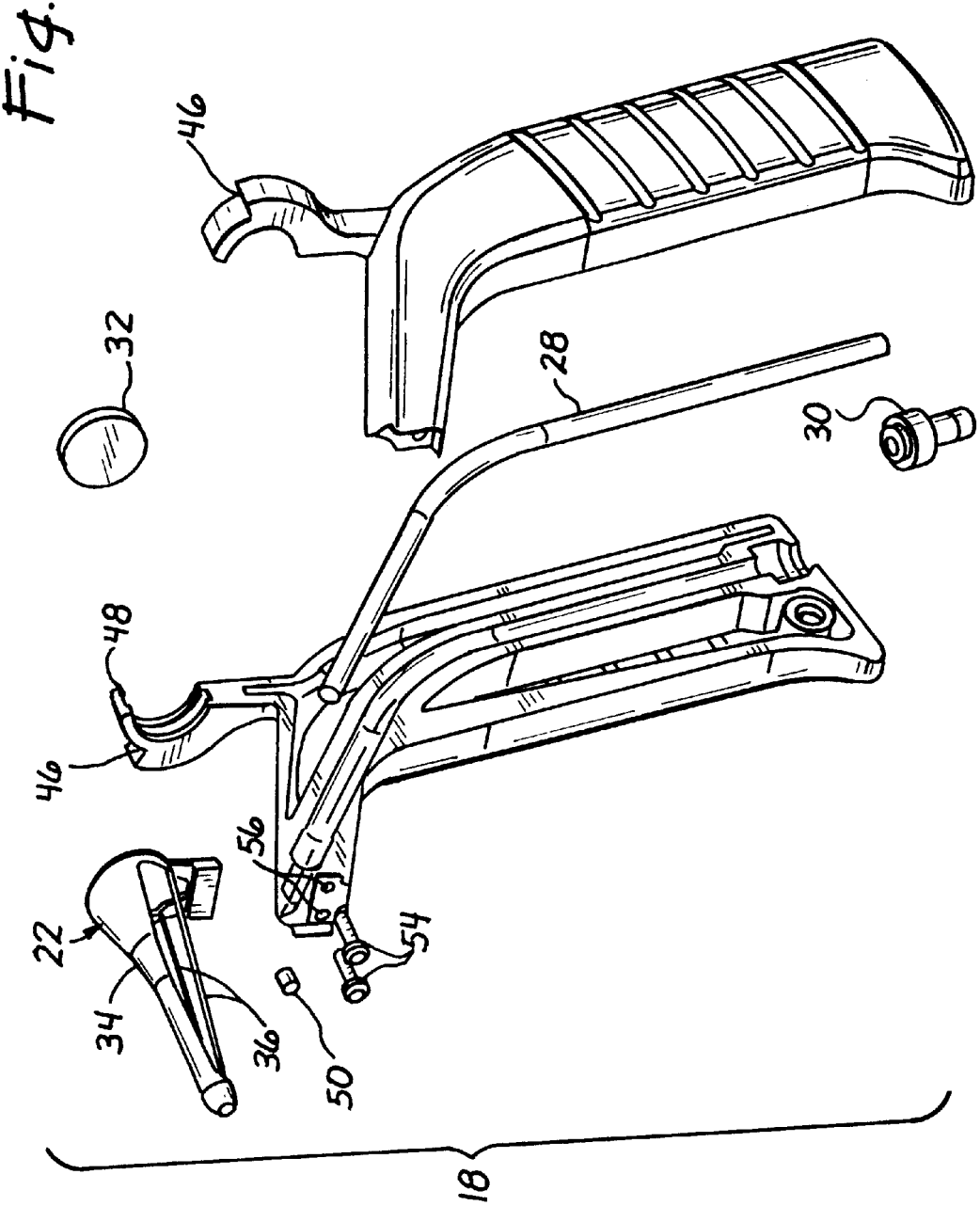

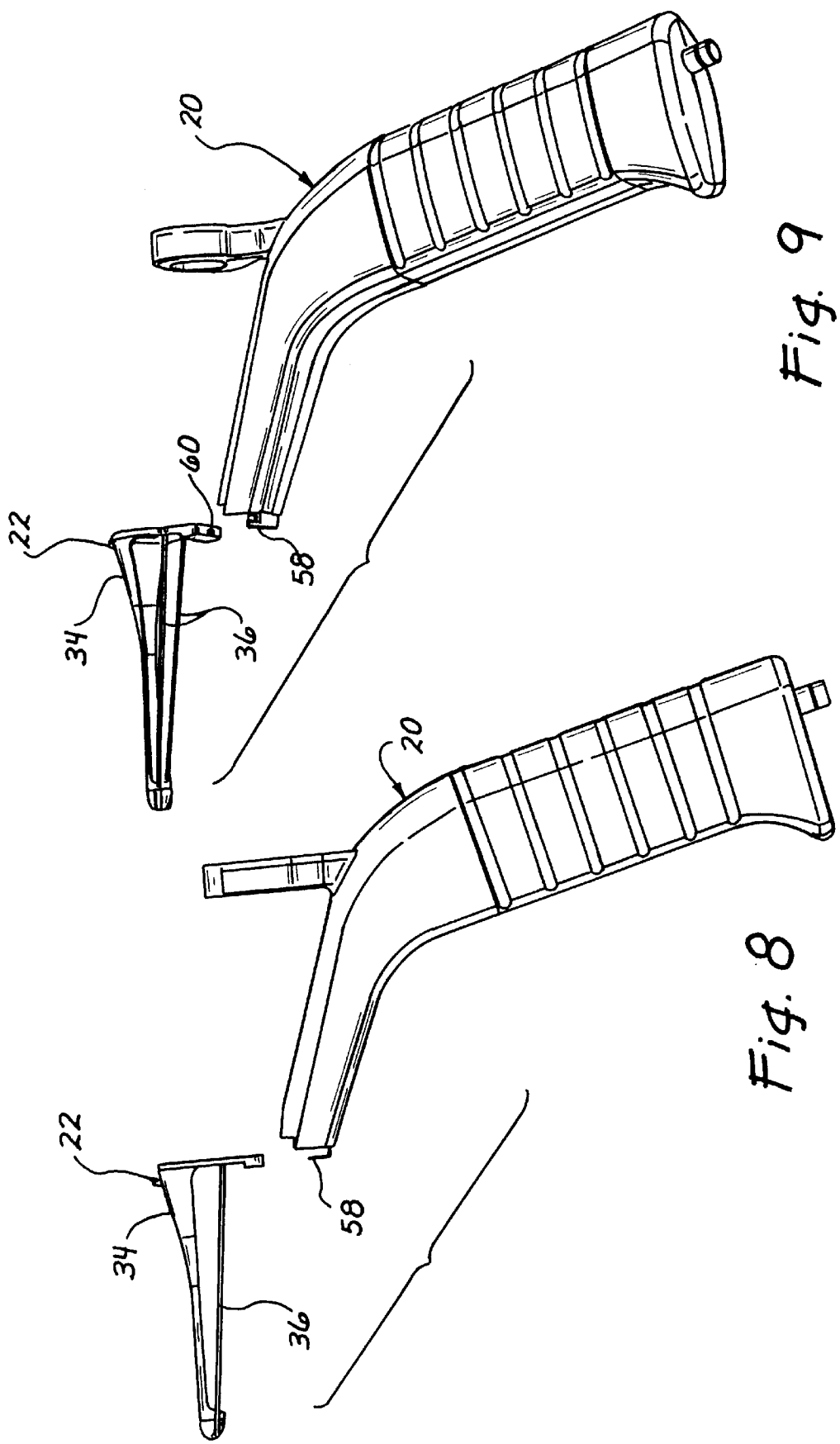

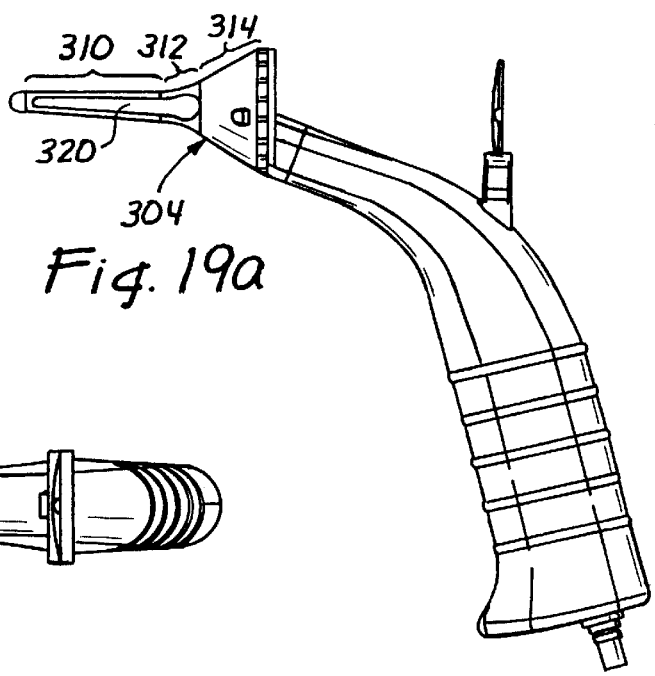
Fig. 19a
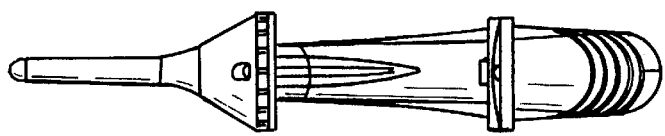
Fig. 19c
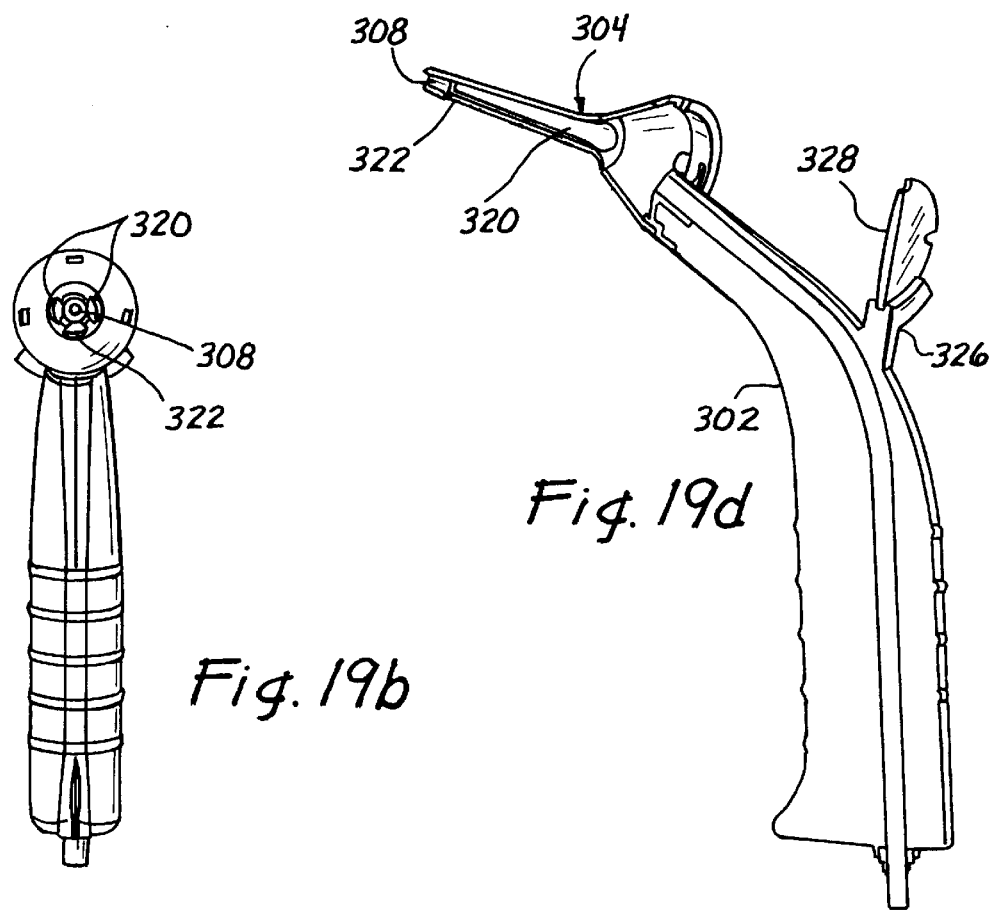
Fig. 19d
Fig. 19b

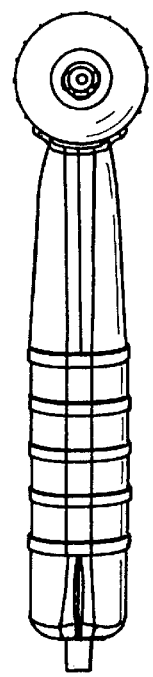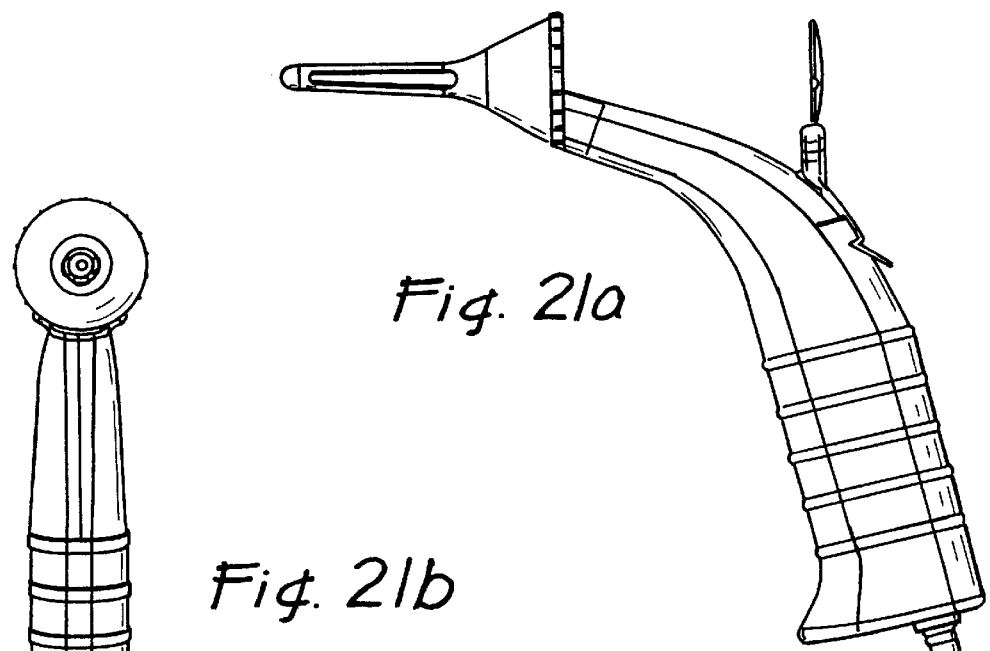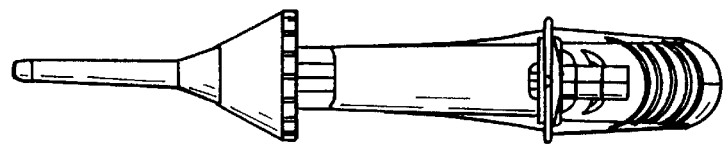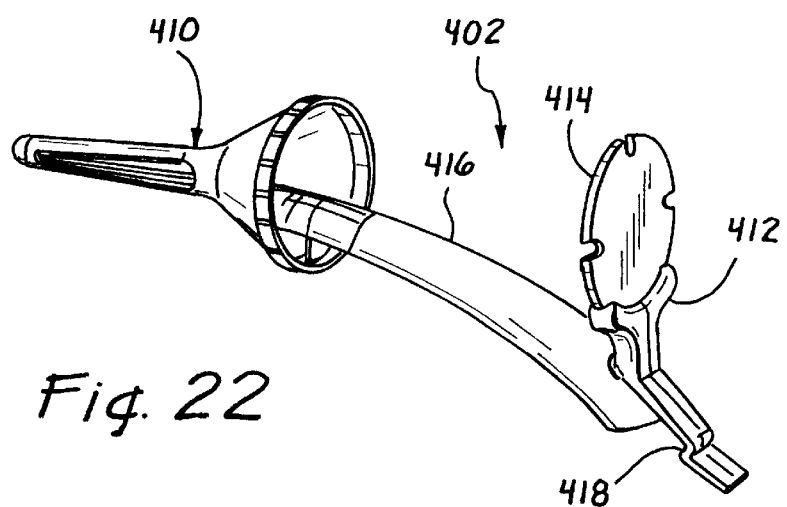

URETHRA SURGICAL DEVICE

This application claims the benefit of priority under 35 U.S.C. §119(e) of U.S. provisional application No. 60/242,945, filed Oct. 24, 2000, U.S. provisional application No. 60/193,666 filed Mar. 31, 2000, and U.S. provisional application No. 60/198,698, filed Apr. 20, 2000.

BACKGROUND OF THE INVENTION

1. Field of the Invention

The present invention relates generally to medical devices and, more particularly, to surgical tools and scopes for viewing and performing surgical operations within body passages.

2. Description of Related Art

A condition known as stress urinary incontinence refers to a functionally insufficient urinary tract of a patient. In a patient having this condition, tissue relaxation of the sphincter mechanism, located at the urinary outflow of the bladder into the urethra, can cause a loss of bladder control. A filler material, such as collagen, can be injected into and adjacent to the urinary sphincter muscle at the bladder neck to "bulk" up the muscle tissue and help ensure adequate closure of the urinary sphincter.

SUMMARY OF THE INVENTION

In accordance with the present invention, a hand-held device or "urethra scope" is provided that is used to expand and visualize tissue within a body lumen. When the body lumen comprises a female urethra, the urethra scope is inserted through the urethra to the bladder neck, and a long needle is used to inject a filler material into and adjacent to the urinary sphincter muscle for the treatment of stress urinary incontinence. The filler material may also be injected along the entire length of the urethra. The urethra scope of the present invention enables visualization of the bladder neck through the female urethra ("transurethral procedure") in order to facilitate injection of the filler material.

The urethra scope of the present invention provides lighting and a clear path to all urethral tissues and the bladder sphincter. The filler material may comprise collagen and/or micro-spheres, such as disclosed in U.S. Pat. No. 5,344,452, or, for example, any other type of injectable bulking agent. In accordance with the present invention, the injection of a urinary bulking agent into the respective tissues serves to fortify the respective tissue structures and re-establish bladder control. The urethra scope and associated methods of operation disclosed herein may be configured for and used on other body passages as well in modified embodiments. The entire injection procedure is preferably performed on an outpatient basis requiring minimal or no sedation of the patient.

The female urethra is about 2.5 to 4 cm long and can be expanded to at least 7–8 mm in diameter. In implementing preferred methods of the present invention, an insertion probe of the urethra scope does not need to be opened or expanded within the urethra. Instead, the insertion probe of the urethra scope is moved distally to expand the urethra walls and is moved proximally to permit the urethra walls to relax inward. The urethra scope of the present invention can also be used in other parts of the body using similar methods of operation, wherever access to and visualization of an anatomical structure in tangential fashion is required.

The urethra scope is designed to be a tissue expansion and visualization device for insertion into tissues and tissue lumens, such as the female urethra. The urethra scope can be manufactured as a reusable or disposable medical instrument or a combination of both. In a preferred embodiment, the device is constructed with a disposable insertion probe (single-use, sterile item comprising or consisting of, for example, plastic, stainless steel, or wire coated with, for example, a polymer or vitreous material), which is attached to a reusable handle (limited use item). The wire construction may comprise, for example, a mesh-shaped conical configuration, for example, wherein the wire is coated with a biocompatible material. In addition to serving as a tissue expansion and visualization tool, the urethra scope can serve as a diagnostic tool to enable physicians to treat their patients with injection treatments, surgical ablation of tissue, tissue biopsies, etc. The advantages of the urethra scope include cost effectiveness, ease of use, decreased likelihood of cross contamination due to sterile disposable cones that are inserted into the urethra, and improved ergonomics and handling. The placement of tangential and distal windows in the insertion probe allows for visualization and treatment of the entire length and circumference of the urethral walls and bladder neck.

The present invention, together with additional features and advantages thereof, may best be understood by reference to the following description taken in connection with the accompanying illustrative drawings.

BRIEF DESCRIPTION OF THE DRAWINGS

FIGS. 6 and 7 illustrate exploded perspective views of the urethra scope of the present invention;

FIGS. 8 and 9 illustrate a first alternative embodiment of the urethra scope;

FIG. 15b is a bottom plan view of the insertion probe of FIG. 15a;

FIGS. 16c and 16d are front and side elevation views, respectively, of the insertion probe of FIG. 15a;

FIGS. 19a and 19b are front and side elevation views, respectively, of the urethra scope of FIGS. 18a–18d; FIG. 19c is a top plan view of the urethra scope of FIGS. 18a–18d;

FIG. 19d is a cutaway perspective view of the urethra scope of FIGS. 18a–18d;

FIGS. 21a and 21b are front and side elevation views, respectively, of the urethra scope of FIGS. 20a–20d;

FIG. 21c is a top plan view of the urethra scope of FIGS. 20a–20d;

FIG. 22 is a perspective view of the insertion probe and lens mount unit of the urethra scope of FIGS. 20a–20d;

DETAILED DESCRIPTION OF THE PRESENTLY PREFERRED EMBODIMENTS

Figure 1:
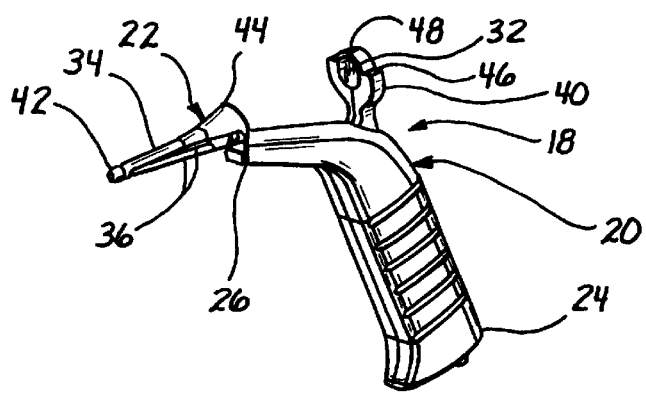
FIG. 1 is a perspective view of a urethra scope in accordance with the present invention.
Figure 2:
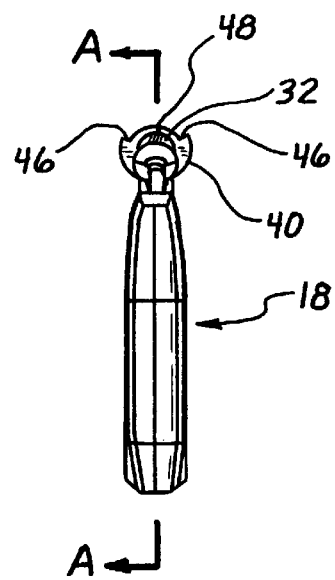
FIG. 2 illustrates a front-elevation view of the urethra scope.

Referring more particularly to the drawings, FIG. 1 illustrates a urethra scope 18 in accordance with the present invention comprising a handle 20 and an insertion probe 22. The handle 20 comprises a proximal end 24 and a distal end 26, and the insertion probe 22 is removably connected to the distal end 26 of the handle 20. FIG. 2 illustrates a front elevation view of the urethra scope 18. The handle 20 of the urethra scope preferably comprises molded plastic and in the illustrated embodiment comprises a "pistol grip" style but is not limited to this construction. Other grip shapes, such as a simple round handles similar to the handles of standard laryngoscopes and otoscopes, may be used as well in modified embodiments. As an alternative to molded plastic, the handle 20 can be machined or formed out of surgical stainless steel for increased durability.

A lens 32 is connected to the handle 20 for providing a magnified view into the insertion probe 22 to aid the vision of a user during a surgical procedure. In a preferred embodiment, the insertion probe 22 is in the shape of a hollow cone or funnel with the large open end aligned with and facing the lens 32 so as to provide a visual passageway through the lumen therein. As illustrated, the lumen or visual passageway is defined within a partially tubular reflective structure 34 that is wider at its proximal end than its distal end, and a pair of spaced posts 36 that extend from the proximal end to the distal end of the reflective structure. The reflective structure 34 and posts 36 are shaped to generally circumscribe a funnel-shaped lumen or visual passageway.

Figure 3A:
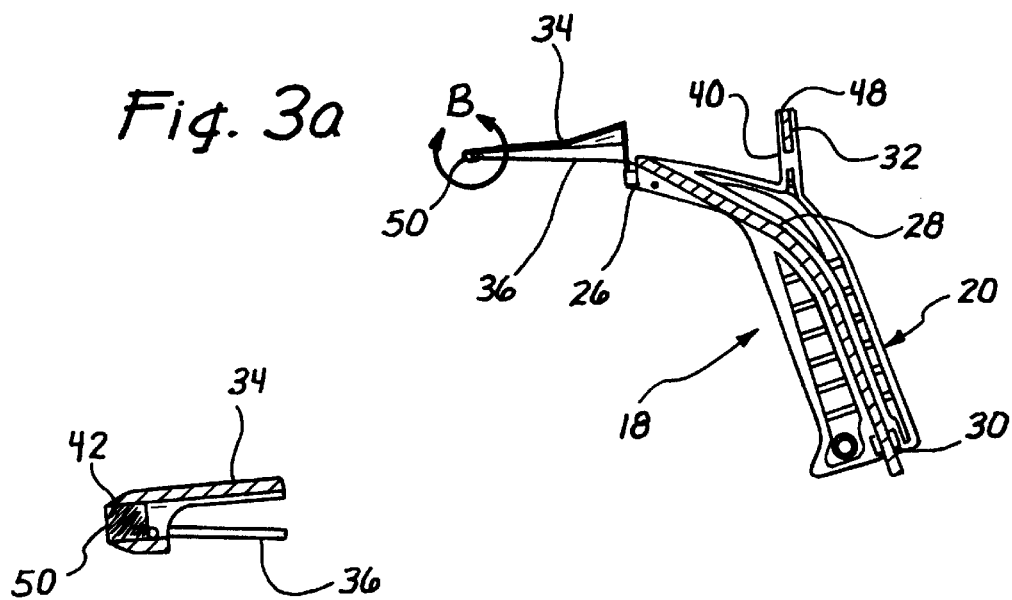
FIGS. 3a and 3b illustrate cross-sectional views of the urethra scope, taken along the line A—A of FIG. 2.
Figure 3B:
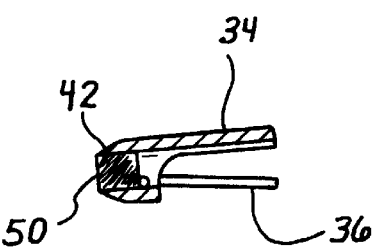

FIGS. 3a and 3b show cross-sectional views of the urethra scope of FIG. 2, taken along the line A—A of FIG. 2. As illustrated in FIGS. 3a and 3b, a light guide 28 is disposed within the handle 20 for carrying light to the distal end 26 of the handle. The light guide 28 preferably comprises a fiberoptic light guide, which is either removably attached to or within the handle to allow for its removal after a procedure or is permanently incorporated into the handle. In a preferred embodiment, the light guide 28 is removably attached to the bottom of the handle at the proximal end 24 in order to avoid or attenuate any interference of a supply cord with the injection procedure. The light guide 28 is preferably removably connected, via an external connector 30, to an external medical light source, such as a light source designed for a cystoscope. Thus, surgeons using an existing cystoscope can remove the fiber optic therefrom and conveniently connect the same fiber optic to the urethra scope. In modified embodiments, a LED, other bulb, or other light source may be incorporated to facilitate direct viewing of the surgical area through the visual passageway of the insertion probe 22.

In the illustrated embodiment, the lens 32 is preferably mounted to an upper surface of the handle 20 to provide magnification of both the visual passageway and anatomical structures within the surgical field. In the illustrated embodiment, the magnification value is approximately 1.66 times normal. In modified embodiments, other magnifications may be used. As presently embodied, the device is fitted with a glass bi-convex 20 mm×500 mm uncoated single lens, wherein 20 mm is the diameter and 500 mm is the focal length. The surgeon can move his or her eye proximally and distally of the lens 32 to adjust his or her focus along the visual passageway within the insertion probe 22. The lens 32 is preferably removable so that it can be easily cleaned, and/or so that a surgeon can choose an unaided, unmagnified view of the visual passageway.

In accordance with the present invention, medical procedures are enabled by the urethra scopes of the present invention. For example, the distal end 42 of the insertion probe 22 can be positioned within the urethra and, while visualizing the urethra through the insertion probe 22, passing a needle around the lens 32 and lens casing 40 into the lumen of the insertion probe 22 to inject a bulking agent into the soft tissue exposed therein. As presently embodied, the lens 32 and lens casing 40 comprise relatively small diameters to facilitate various needle insertion angles and orientations. The small diameter of the lens casing 40 thus helps to avoid interference with the injection needle or any other surgical instrument during the procedure and allows for greater treatment flexibility on the physician's part. In the injection treatment of urinary incontinence in accordance with the present invention, it may be beneficial to inject submucosally (beneath the mucosa) along the entire length of the urethra, using a parallel-placement technique of the injection needle submucosally along the outer diameter of the urethra. The relatively small diameter of the lens 32 thus allows for performance of this improved injection procedure. A relatively large lens 32 and/or casing 40 may not sufficiently allow for a needle to be orientated around the lens casing 40 and through the insertion probe 22, for proper parallel-placement and injection of bulking agent along the entire length of the urethra.

In the illustrated embodiment, the proximal portion 44 of the insertion probe 22 extends radially outwardly at a steeper angle than the rest of the insertion probe 22 (i.e., the proximal portion 44 has a larger taper angle if conical, or has a more pronounced curvature if otherwise shaped, than the distal end 42). The steeper-angled proximal portion 44, in combination with the relatively small diameter of the lens casing 40, help to facilitate various needle insertion angles and orientations. In addition to the proximal portion 44 of the insertion probe 22 providing greater needle maneuverability, the remaining conical or flared portion of the insertion probe 22 provides further needle maneuverability, while also serving to expand and contract the body lumen, e.g., urethra, through distal and proximal movement. Additionally, the two conical sections of the insertion probe 22, i.e., the proximal portion 44 and the remaining portion, serve to focus the light from the light guide 28 through the insertion probe 22 and toward the distal end 42 of the insertion probe 22. In the illustrated embodiment, two platforms 46 and a notch 48 are provided in the lens casing 40 for alignment and/or stabilization of the insertion needle or other surgical instrument. In the illustrated embodiment, the casing 40 comprises two halves that fit together to encircle the lens 32. As an example of use, the two platforms 46 can help to align the needle for the two and ten o'clock position injections of filler material, and the notch 48 can help to align the needle for the six o'clock position injection of filler material. In modified embodiments, either or both of the platforms 46 and notch 48 can be omitted or positioned at different locations on the casing 40. In another modified embodiment, the notch 48 is omitted and the lens casing only encircles the bottom half or the lens 32. In this embodiment the lens can be lifted up and out of the lens casing and the two upper ends of the lens casing can serve as the platforms for optionally aiding in needle positioning. The top of the lens 32 may be notched in this embodiment for optionally aiding in needle positioning.

Figure 15A:
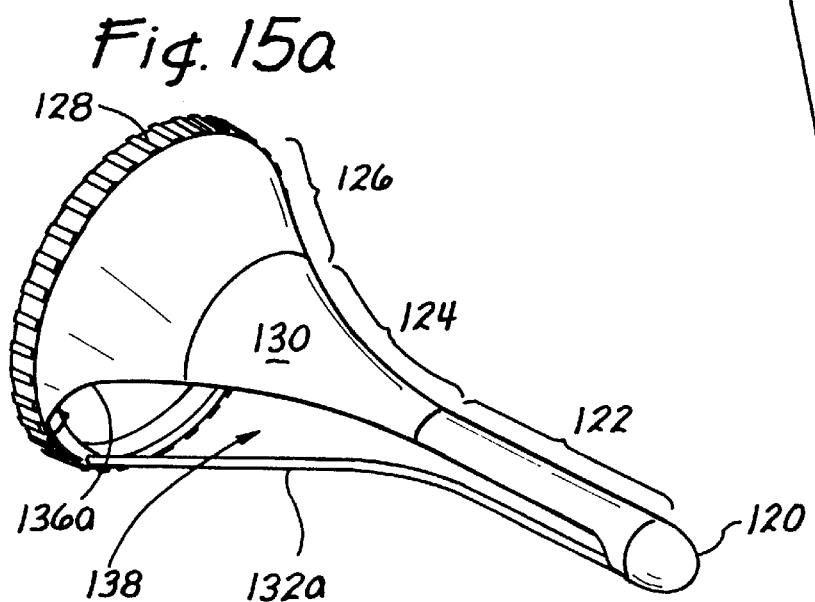
FIG. 15a is a perspective view of the insertion probe of the urethra scope of FIG. 14.
Figure 15B:
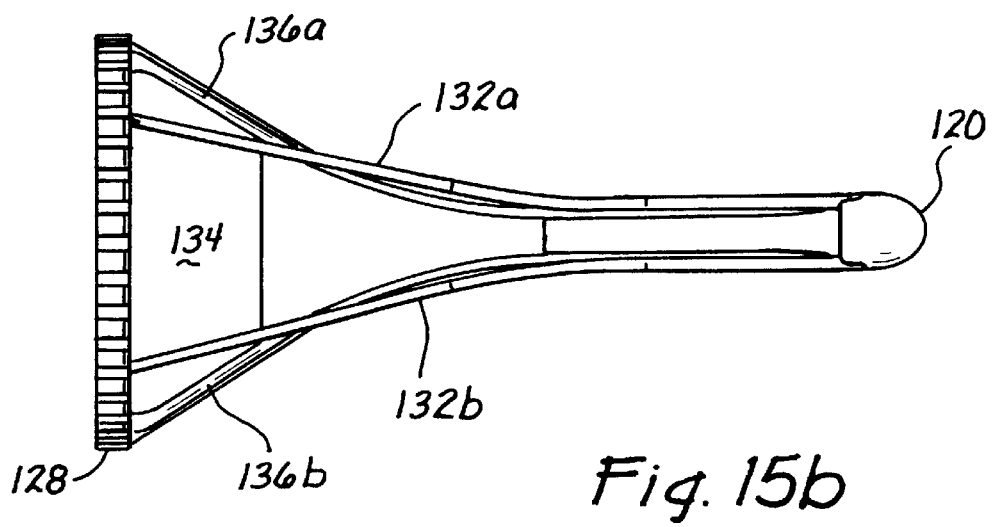

In a modified embodiment, notches or slots may be placed in the proximal portion 44 of the insertion probe 22 for stabilization of the insertion needle, such as shown, for example, in FIGS. 15a and 15b. In other modified embodiments, the lens 32 may be removed altogether and/or one or both of the conical portions of the insertion probe 22 may be formed into a cylindrical or other shape instead. For example, in one modified embodiment the conical portion located distally of the proximal portion 44 may be formed as a cylinder instead of a cone. In another modified embodiment the proximal portion 44 may be formed to have the same angle of radial expansion as the proximal portion of the insertion probe 22. If a larger lens and casing are used, windows or slots, such as radially extending slots, can be placed on or through the lens for the insertion and stabilization of the injection needle. For example, slots or perforations may be placed at the two, ten and twelve o'clock positions of the lens.

Light transmitted through the light guide 28 is directed toward the side and under surfaces of the reflective structure 34 of the insertion probe 22. The reflective structure 34 serves as a reflector to disperse the light from the light guide 28 into the anatomic structure. In a preferred embodiment the insertion probe 22 comprises medical grade plastic (e.g., polycarbonate) formed by injection or compression molding. In another embodiment, part or all of the insertion probe 22 comprises a clear, medical grade plastic. The under surface of the upper portion of the insertion probe is covered with a polished metal as the reflecting surface in one embodiment. In modified embodiments, this under surface may comprise another coating or may merely comprise a smooth plastic. In other modified embodiments, part or all of the insertion probe 22 can comprise surgical stainless steel.

In yet another modified embodiment, a light source is routed into or partially through the reflective structure, and the reflective structure is formed of a clear or light transmitting material, to emit light along the length of the reflective structure. A purpose of this structure is to route additional light toward the distal end of the insertion probe. Alternatively, the reflective structure can comprise one or more posts formed of a transparent material for receiving and emitting light along their lengths. In another embodiment, the insertion probe can comprise a number of posts, for example, three posts (with a smaller or no reflective structure), wherein all three of the posts receive and emit light along their lengths. In the embodiments of this paragraph, the entire insertion probe may be formed, for example, of clear plastic for transmitting light.

A distal lens 50 can be fitted to the distal end 42 of the insertion probe 22. This distal lens 50 serves to enable visualization of the tissue structures located in front of the insertion probe 22. The distal lens 50 can be particularly important in order to identify the bladder neck located at the transition area between the bladder and the urethra. In modified embodiments, the distal lens 50 may comprise a fish-eye lens, or may be omitted altogether. In a preferred embodiment, the distal lens is omitted but the aperture is maintained to allow distal vision for the surgeon.

The two posts 36 can be, for example, integrally formed of a plastic with the rest of the insertion probe 22, using an injection molding process. In modified embodiments, the two posts 36 can comprise a rigid material such as surgical stainless steel. In one embodiment, a single stainless steel rod is bent in half at the distal tip of the insertion probe 22 to form the two posts 36, which are then fitted into the remaining plastic or stainless steel insertion probe 22. In the illustrated embodiment, a proximal end of the distal lens 50 is larger than a distal end and/or the lumen of the distal end 42 is slightly tapered or otherwise reduced in size, so that the distal lens 50 can be placed or press fitted, by movement in a distal direction, into the distal end of the insertion probe 22. The stainless steel rod is then bent around the proximal end of the distal lens 50 to thereby contact and secure the distal lens 50 within the distal end 42.

The illustrated embodiment provides, but is not limited to, the two posts 36 being formed at the four and eight o'clock positions of the cross-section in order to gradually expand the urethra during insertion. When the urethra scope 18 has been inserted into the urethra and tissue has prolapsed into the windows on adjacent sides of the two posts 36, the urethra walls will generally prolapse into the windows along the length of the urethra. The prolapsed tissue will be well illuminated within the lumen of the insertion probe 22, and can be seen by the surgeon under the magnification of the lens 32. A surgeon can then inject bulking agent into or along the length of each section of prolapsed tissue within each window to form, for example, a longitudinally extending enhanced-tissue structure of bulking agent. Three longitudinally extending enhanced-tissue structure injections may be performed, for example, at the two, six and ten o'clock positions.

In accordance with one aspect of the present invention, one or more of the longitudinally extending enhanced-tissue structure injections may be performed without any or without substantial movement of the urethra scope. The urethra scope may be rotated along the longitudinal axis of the insertion probe 22, and/or may be slightly pivoted off of the longitudinal axis, for allowing the surgeon to inject bulking agent into different locations. In addition to implanting longitudinally extending enhanced-tissue structures along the entire length of the urethra, more conventional injections may be implemented, such as an injection of bulking agent into and adjacent to the urinary sphincter muscle only.

In accordance with one aspect of the present invention, it is recognized that a nerve is typically present at about the twelve o'clock position of the urethra wall. Accordingly, the reflective structure 34 is preferably formed in accordance with this aspect of the invention to cover the twelve o'clock position and general vicinity to prevent surgeons from accidentally damaging this nerve. For example, the reflective structure in the illustrated embodiment spans from the two to ten o'clock positions, and the surgeon can be instructed not to rotate the urethra scope along the axis of the insertion probe 22 so that the twelve o'clock position remains protected.

The visual passageway through the insertion probe 22 can provide a very natural and intuitive operating environment for the surgeon, as distinguished from the surgeon observing the surgical area through, for example, expensive video monitors which are commonly used in combination with standard cystoscopes. The design of the insertion probe 22 serves to retract tissue and create space due to the conical (e.g., increasing diameter) shape and the position and orientation of the two posts 36 located under it. Proximal and distal movement of the insertion probe 22 can be implemented by the surgeon to increase and decrease the diameter of the tissue or body lumen, e.g., urethra, to thereby allow the surgeon greater maneuverability, manipulation and access during the surgical procedure, compared to a prior-art devices. The windows formed between the two posts 36 facilitate the prolapse of tissue into the lumen of the urethra scope. The conical shape of the insertion probe 22 can enable the surgeon to treat various-sized urethras with a single size, since larger-diameter urethras can be dilated with a deeper insertion of the insertion probe 22 and smaller-diameter urethras can be dilated with a shallower penetration of the insertion probe 22. Moreover, a smaller urethra, which may require less penetration of the insertion probe 22, may not have a lumen that is as long as a larger-diameter urethra. Furthermore, in the illustrated embodiment, the windows formed by the reflective structure 34 and the two posts 36 are smaller at the distal end of the insertion probe 22 than at the proximal end of the insertion probe 22. Thus, smaller urethras will have smaller windows formed by the insertion probe 22 for proportionately smaller prolapses of the tissue into the lumen of the insertion probe 22.

In modified embodiments, the insertion probe 22 may comprise windows of various numbers, sizes and shapes disposed therein. For example, the reflective structure 34 may form a complete cone or cylinder, with one or more windows being formed therein. In a modified embodiment, the reflective structure 34 may form a complete cone or cylinder made of a mesh screen, wherein the needle can be inserted through the screen mesh at any location. In this embodiment, the screen may be selected to have sufficient rigidity or thickness, or structural members may be used to support the screen mesh.

Figure 4:
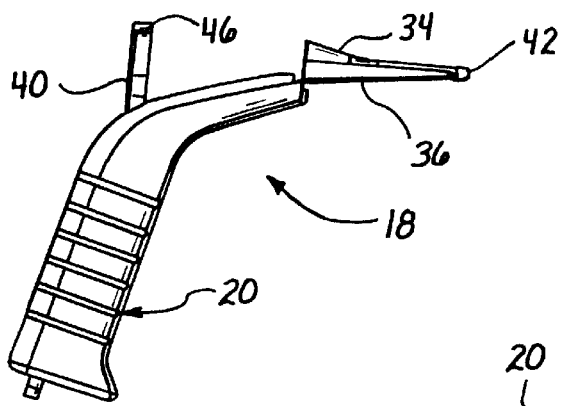
FIG. 4 illustrates a side-elevation view of the urethra scope.
Figure 5:
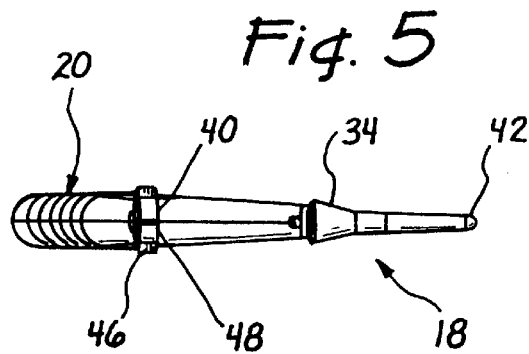
FIG. 5 illustrates a top plan view of the urethra scope.
Figure 7:
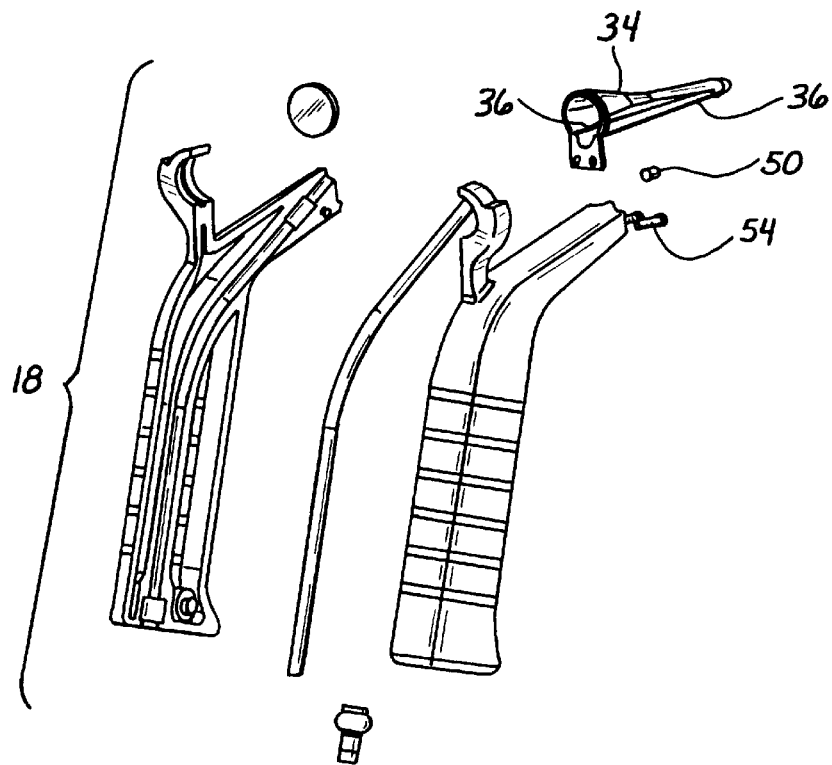

FIG. 4 shows a side-elevation view of the urethra scope 18; FIG. 5 shows a top plan view of the urethra scope 18; and FIGS. 6 and 7 show exploded perspective views of the urethra scope 18 of the illustrated embodiment. As shown in the illustrated embodiment of FIGS. 6 and 7, the insertion probe 22 is secured to the handle 20 with two screws 54 which are threaded through corresponding apertures in the insertion probe 22 and handle 20. Another embodiment is shown in FIGS. 8 and 9, wherein the insertion probe 22 is snap-fitted or otherwise removably secured to the handle 20 with, for example, a male-female interlocking assembly. A rectangular pin 58 on the handle 20 fits into a rectangular aperture 60 on the insertion probe 22. In other embodiments, a quick-disconnect type of assembly may be used to removably secure the insertion probe 22 to the handle 20.

Figure 10A:
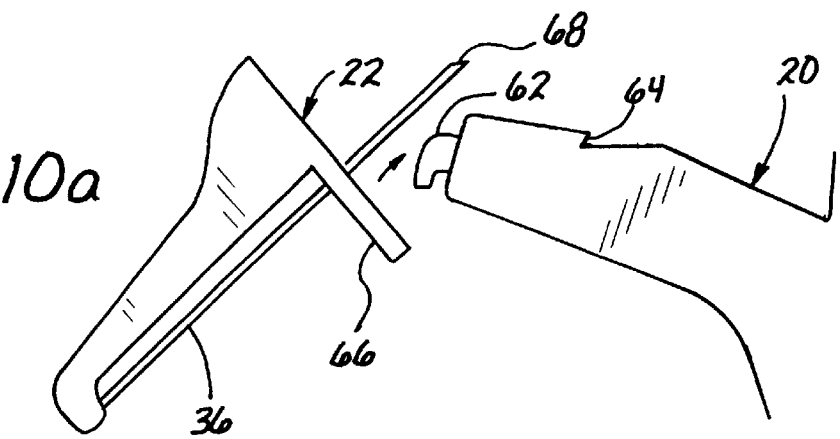
FIGS. 10a–10c illustrate a second alternative embodiment of the urethra scope.
Figure 10B:
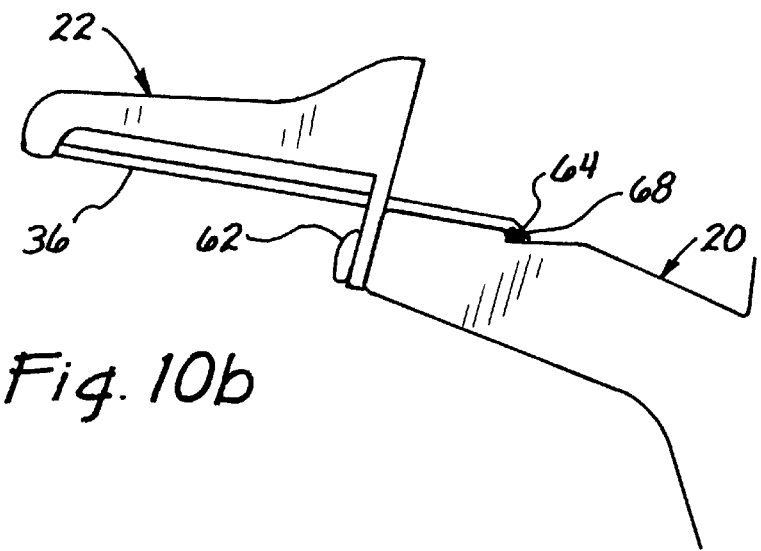
Figure 10C:
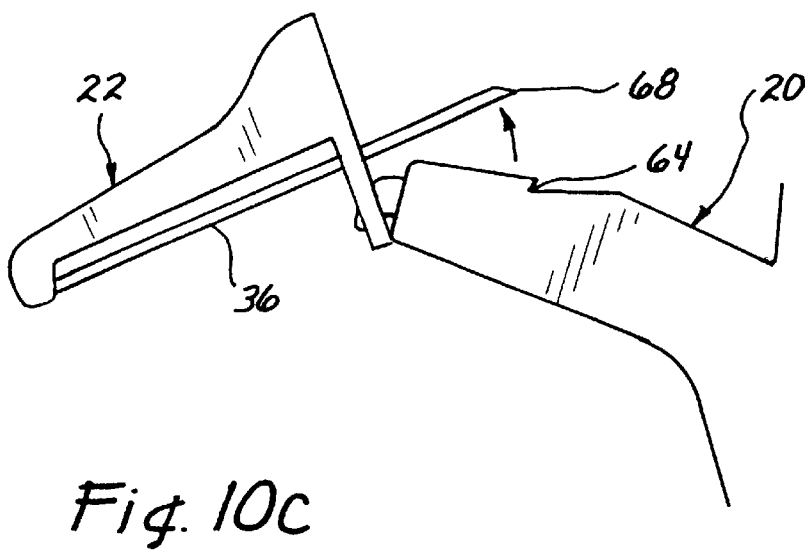

Another snap-fit embodiment is illustrated in FIGS. 10a–10c, wherein the handle 20 of the urethra scope comprises a protrusion 62, preferably having a rectangular cross section and a hook shape. The handle 20 further comprises a notch 64. The insertion probe 22 comprises a rectangular aperture 66, which is adapted to fit around and pivot about the protrusion 62. The two posts 36 of the insertion probe 22 are extended proximally behind the insertion probe 22 and terminated with a transverse member 68 connecting the two posts 36. In operation, the rectangular aperture 62 will pivot about the protrusion 62 and swing into place. Just before the insertion probe 22 is finally seated, the transverse member 68 will contact and fit into the notch 64 in the handle 20, to thereby secure the insertion probe 22 to the handle 20. To remove the insertion probe 22, the transverse member 68 is lifted up and out of the notch 64. Indentions may be formed on the two sides and/or proximally of the groove 64 to allow for removal of the seated transverse member 68. After the transverse member 68 is removed from the notch 64, the insertion probe 22 is rotated and removed from the rectangular protrusion 62.

Figure 11:
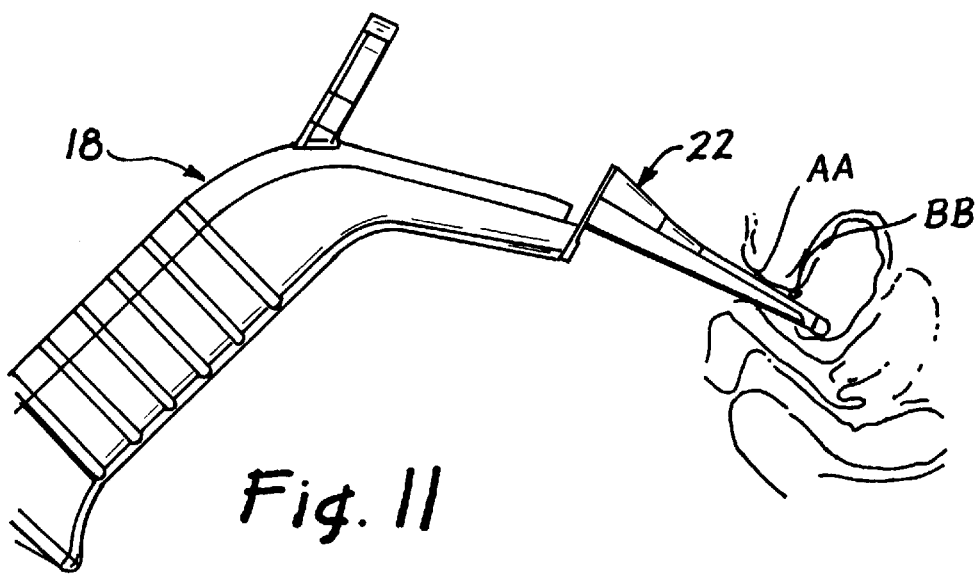
FIG. 11 illustrates the urethra scope of the present invention inserted into a female urethra.

FIG. 11 illustrates an insertion of the urethra scope 18 into a female urethra. In the presently preferred embodiment, a needle (not shown) is preferably not present during insertion of the urethra scope 18 into the urethra. Although not illustrated, the urethra scope 18 of the present invention may be used in a variety of medical applications, including various surgical procedures within, for example, the urethra. With the needle not present or retracted, the urethra scope 18 can be advanced through the urethra and urinary sphincter muscle into the bladder and, subsequently, withdrawn slightly to align, for example, the distal tip 42 of the urethra scope 18 just proximally of the urinary sphincter muscle. The physician can visually inspect the inner wall of the urethra to ensure an optimal opening of the lumen of the urethra.

Figure 12A:
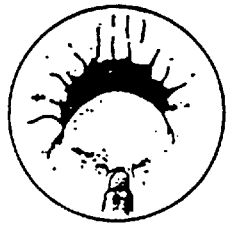
FIGS. 12a–12d illustrate various injection procedures that may be performed using the urethra scope of the present invention.
Figure 12B:
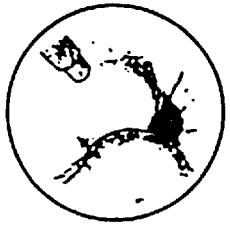
Figure 12C:

Once the physician has positioned the urethra scope 18, he or she can insert a needle through the urethra scope 18 and into the tissue to be treated, for subsequent injection of bulking agent into the tissue. In the illustrated embodiment, bulking agent is first injected into the six o'clock position to form a first mucosa bulge as shown in FIG. 12a. The surgeon may choose, for example, to use the notch 48 for positioning and/or stabilizing the needle during this procedure. As shown in FIGS. 12b and 12c, bulking agent is next injected in the illustrated embodiment at ten o'clock to form a second mucosa bulge and, subsequently, injected at two o'clock to form a third mucosa bulge. The surgeon may choose, for example, to use the platforms 46 for positioning and/or stabilizing the needle during these procedures.

Figure 12D:

The user can inspect the three (or greater or lesser number of) mucosa bulges via the illuminated visual passageway of the urethra scope 18. Various viewing angles can be formed, by changing the position and orientation of the urethra scope 18. The urethra scope 18 can be advanced up to, within, and beyond (distal) of the three mucosa bulges for visual and tactile inspection. The urethra scope 18 of the present invention facilitates tactile testing of the mucosa bulges, via, for example, opening of the passageway between the mucosa bulges by distal movement of the insertion probe 22, to ensure surgical success. If for example one or more of the mucosa bulges are determined by the surgeon to be too large or non-displaceable, the surgeon can massage and redistribute the bulking agent with the insertion probe 22 for a more functionally suitable distribution of the bulking agent. The insertion probe 22 may be rotated, for example, to place the reflective structure 34 and/or one of the two posts 36, onto one or more of the mucosa bulges or longitudinally-extending enhanced-tissue structures for massage and/or redistribution of the bulking agent therein. FIG. 12d illustrates a variation of the bulking-agent injection procedure, wherein the needle is inserted into tissue outside of the urethra and advanced through the urethra walls to the injection site. Although not shown, the urethra scope 18 of the present invention can be used with this procedure as well to allow the surgeon to visualize the swelling of the urethra tissue as bulking agent is injected and, subsequently, to facilitate tactile testing and/or redistribution of bulking agent as described above.

In a presently preferred embodiment, after the three mucosa bulges are formed the insertion probe 22 can be positioned so that the distal tip thereof is just proximal of the area including and/or adjacent to the three mucosa bulges. The surgeon can visualize, via the distal lens 50 and the windows between the reflective structure 34 and the two posts 36, the full surface of each longitudinally extending tissue prolapse, and thus the ensuing injections and structure can be performed under the direct vision of the surgeon. As the insertion probe 22 is advanced distally and retracted proximally, the surgeon can further inspect the mucosa bulges through the windows formed between the reflective structure 34 and the two posts 36. The surgeon can add additional bulking agent into the prolapsed tissue areas at, for example, six, ten and/or three o'clock, or at other angular positions.

Figure 13:
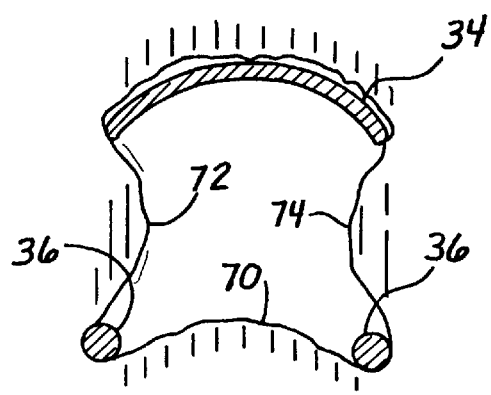
FIG. 13 shows a cross-sectional view of the urethra scope within a female urethra in accordance with the present invention.

FIG. 13 illustrates a cross-sectional view of the insertion probe 22 within the urethra of a patient. A first section of prolapsed tissue 70 is present between the two posts 36 at the six o'clock position. A second section of prolapsed tissue 72 is present between one of the two posts 36 and the reflective structure 34 at the ten o'clock position, and a third section of prolapsed tissue 74 is present between the other post 36 and the reflective structure 34. In accordance with one embodiment of the present invention, a needle can be inserted through one or more of the entire sections of prolapsed tissue 70, 72, 74, entering at point AA (FIG. 11) and terminating within the tissue at point BB (FIG. 11) near the urinary sphincter. Bulking agent can be injected at point BB and, subsequently, injected at one or all of the points between point AA and point BB as the needle is withdrawn. Thus, for example, three longitudinally extending enhanced-tissue structures can be generated at, for example, the six, ten and two o'clock positions.

In modified embodiments of the invention, one, three, or more posts 36 may be used, and the number/configurations/positionings of mucosa bulges may be increased or decreased alone, or in combination with various numbers/configurations/positionings/lengths of longitudinally-extending enhancedtissue structures. The size and radial circumference of the reflective member 34 may also be varied. In addition to changing or modifying the number of posts 36, the shapes and/or configurations of the posts 36 may be changed. For example, the curvature, dimensions and/or spacings of one or both of the posts 36 can be modified to affect, inter alia, the amount and shape of the prolapses of tissue therebetween. One or more of the posts 36 may be configured, for example, to have the same spacing therebetween at every point along all or a portion of a length of the insertion probe.

Figure 14:
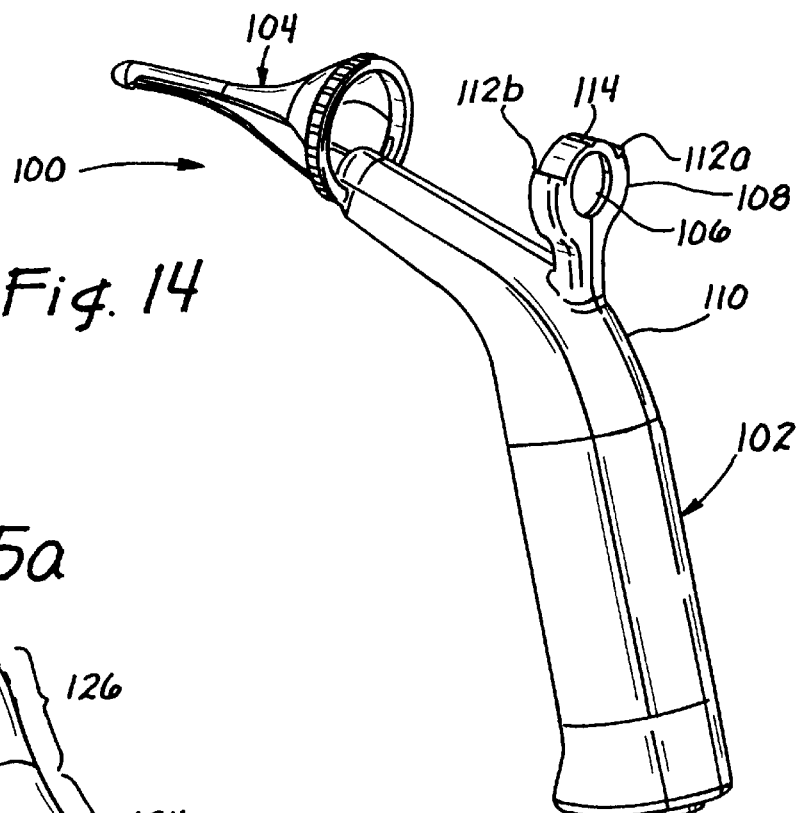
FIG. 14 is a perspective view of a further urethra scope in accordance with the present invention.

FIGS. 14–16 illustrate a urethra scope 100 of the present invention that is in many respects similar to the urethra scope 18 shown and described with respect to FIGS. 1–9. The urethra scope 100 comprises a handle 102 and an insertion probe 104. As before, the handle 102 preferably comprises a molded plastic "pistol grip" style, though the construction is not limited to that style, and the insertion probe 104 is removably connected to the handle 102. A lens 106 is provided within a lens bracket 108 that extends from an elbow 110 of the handle 102 such that the lens 106 is generally axially aligned with the insertion probe 104. The bracket 108 includes two platforms 112a, 112b and a central notch 114 for use in stabilizing an injection needle. In this embodiment, therefore, the insertion probe 104 may be detached from the handle 102 and disposed, but the handle and lens mounting bracket 108 can be reused.

The insertion probe 104 is seen isolated in FIGS. 15a, 15b, 16c and 16d, and includes a closed distal tip 120, a distal insertion length 122 (which is preferably slightly tapered), a first tissue expanding portion 124, and a second wider tissue expanding portion 126. A ring 128 having a plurality of short ribs thereon defines the proximal end of the insertion probe 104. The insertion length 122, and expanding portions 124, 126 are defined by an upper solid member 130, and a lower pair of tissue spreading posts 132a, 132b. The solid member 130 is partly tubular (i.e., not flared) in the insertion length 122, curvilinearly flared in a first tissue expanding portion 124, and substantially conical in the second tissue expanding portion 126. The tissue spreading posts 132a, 132b generally conform to the shape of the solid member 130, but as seen best in FIGS. 15b and 16a begin to flare in the insertion length 122 and have slightly less exaggerated curvatures along their lengths.

The solid member 130 desirably has partial annular cross-sections along its entire length, gradually increasing through the expanding portions 124, 126. Consequently, an inner wall 134 (FIG. 15b) of the solid member 130 partially defines a lumen or channel through the insertion probe 104. Elongated side edges 136a, 136b of solid member 130 define the extent of a visibility window 138 enabling tissue visualization and treatment with the urethra scope 100. The tissue spreading posts 132a, 132b extend generally longitudinally across the visibility window 138. The front elevation view of FIG. 16c best illustrates the extent of opening of the visibility window 138, and the relative positioning of the tissue spreading posts 132a, 132b. In the exemplary embodiment, the tissue spreading posts 132a, 132b are oriented symmetrically about a longitudinal axis of the insertion probe 104 and are spaced apart by an angle of about 60 degrees.

Figure 16A:
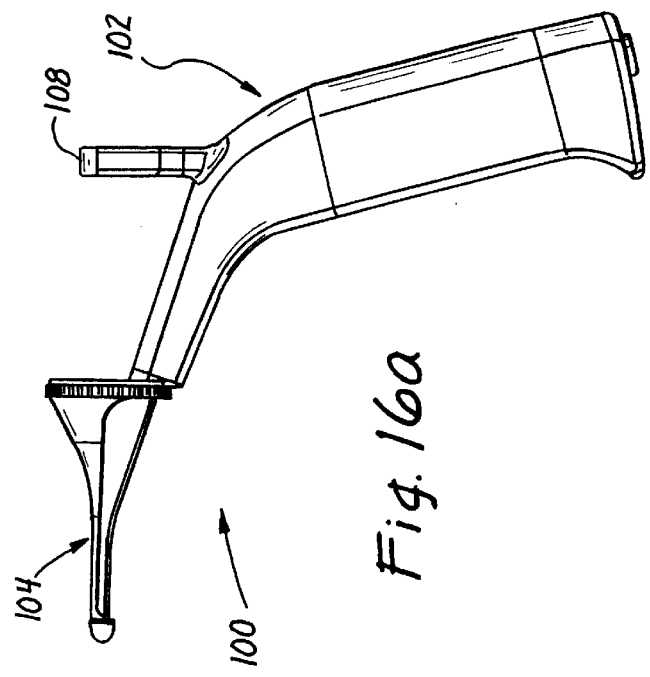
FIGS. 16a and 16b are side and front elevation views, respectively, of the urethra scope of FIG. 14.
Figure 16B:
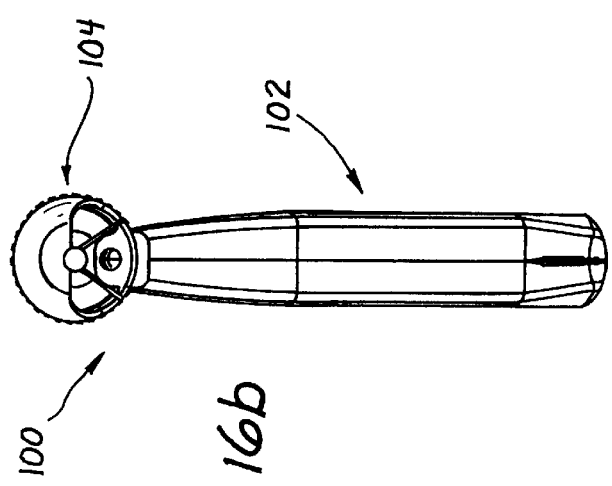
Figure 16D:
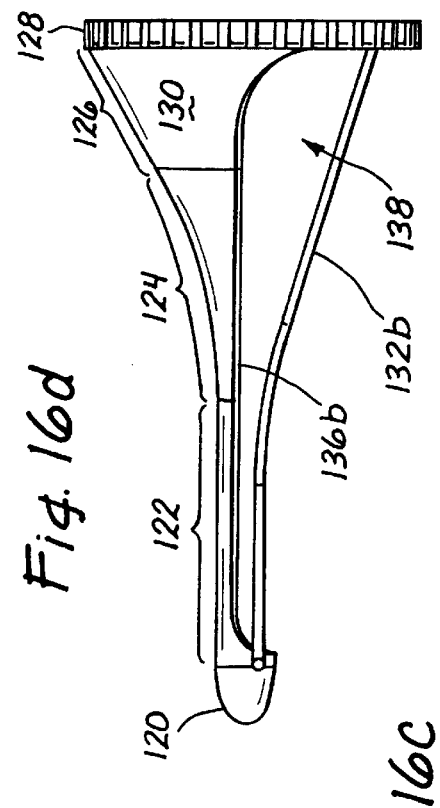
Figure 16C:
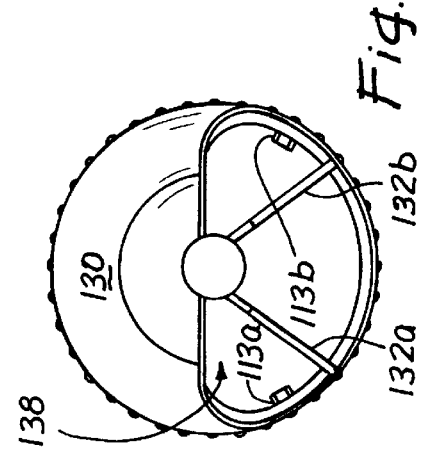

As described above with respect to earlier embodiments, the urethra scope 100 functions by inserting the probe 104 into the urethra until the distal tip 120 is located just outside the sphincter muscle of the urethra. The soft tissue of the surrounding urethra tends to prolapse into the visibility window 138 but is prevented from fully entering the window by the tissue spreading posts 132a, 132b. A surgeon can then inject bulking agent along a partial or full length of each section of prolapsed tissue within the window to form, for example, a longitudinally extending enhanced-tissue structure comprising bulking agent. The needle used for injecting the bulking agent can be positioned on one of the platforms 112a, 112b, or on the central notch 114, and is inserted through the proximal ring 128 into the lumen of the injection probe 104. As can be seen in FIG. 16c, the insertion probe 104 preferably comprises at least one notch and, more preferably, two notches or platforms 113a and 113b formed on the inner surface of the insertion probe 104 and, more preferably, formed on the inner surface of the proximal ring 128. More than two notches can be constructed in modified embodiments. The two notches 113a and 113b operate similarly to the notches 112a and 112b of FIG. 14, for example, by aiding in the placement of, for example, an injection needle, and may comprise alternative forms and locations within the insertion probe 104 in modified embodiments so long as they provide a function of needle stabilization. The ribs on the exterior of the proximal ring 128 may help to facilitate rotationally positioning of the probe 104 by a surgeon. As described previously, a source of illumination is desirably provided at the distal tip of the handle 102 so that it illuminates the visibility window 138 of the insertion probe 104, and the inner surface of the upper solid member 130 is preferably constructed to have a reflective surface or, alternatively, to be transparent.

Figure 17A:
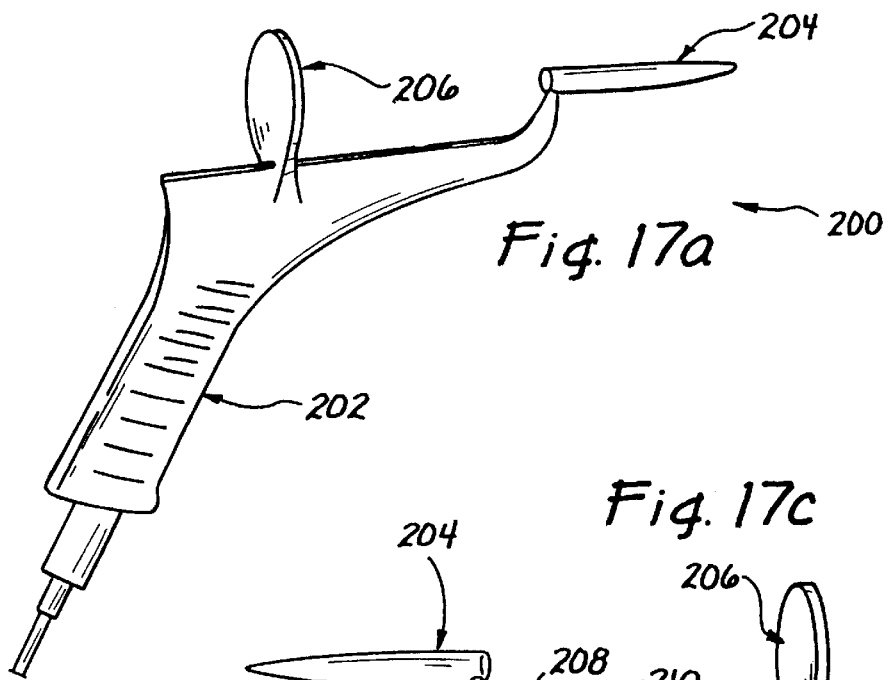
FIGS. 17a–17f are various views of an alternative urethra scope in accordance with the present invention having an insertion probe defined by a partially tubular wall and at least one single tissue retraction post.
Figure 17C:
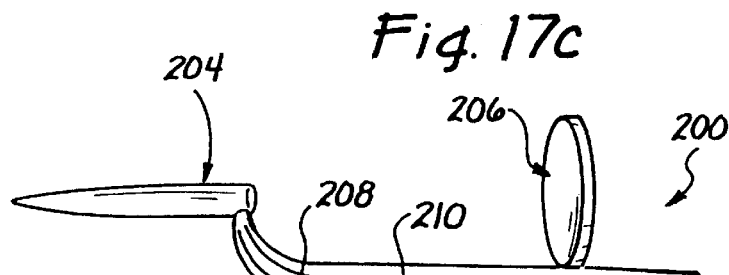
Figure 17B:
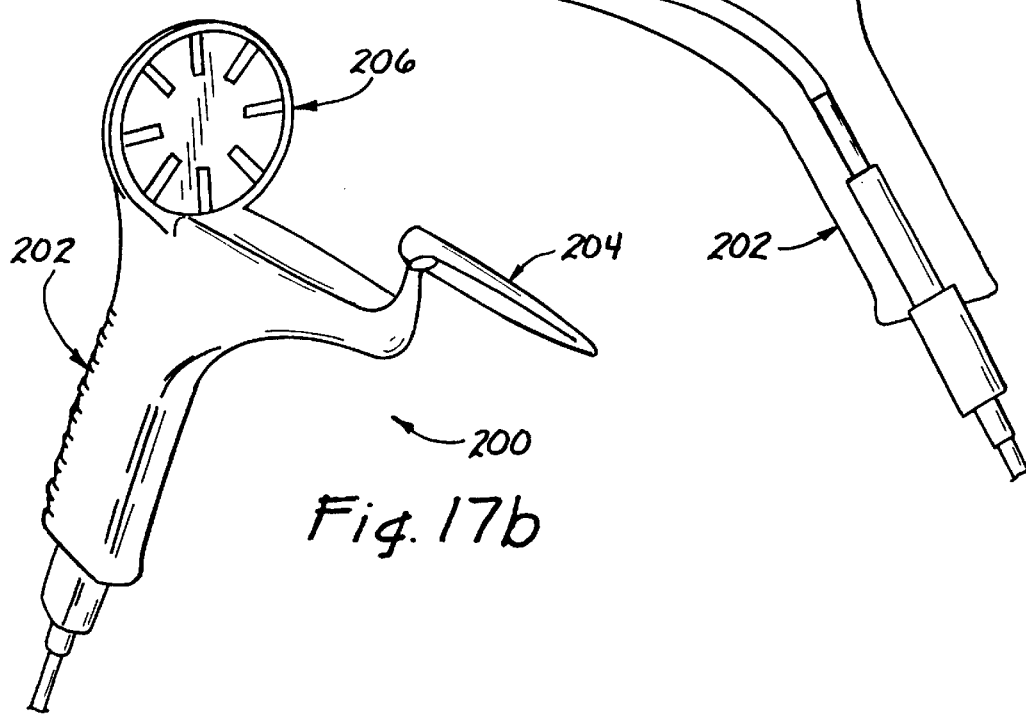
Figure 17E:
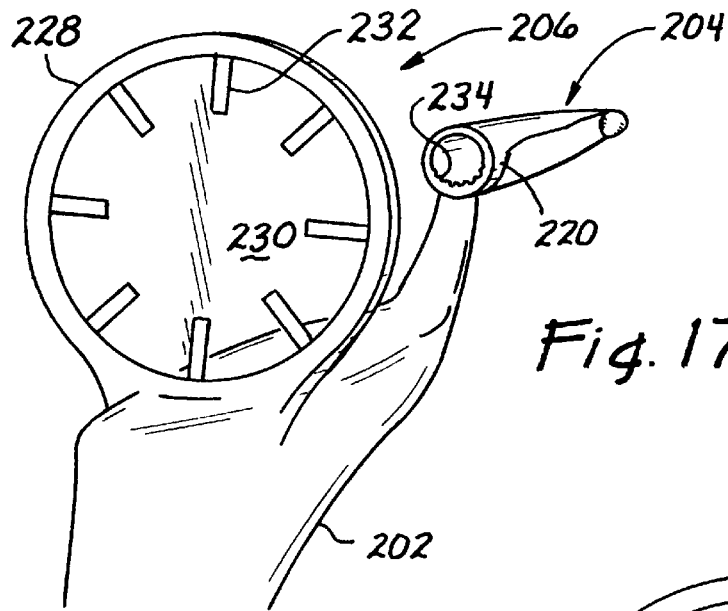
Figure 17F:
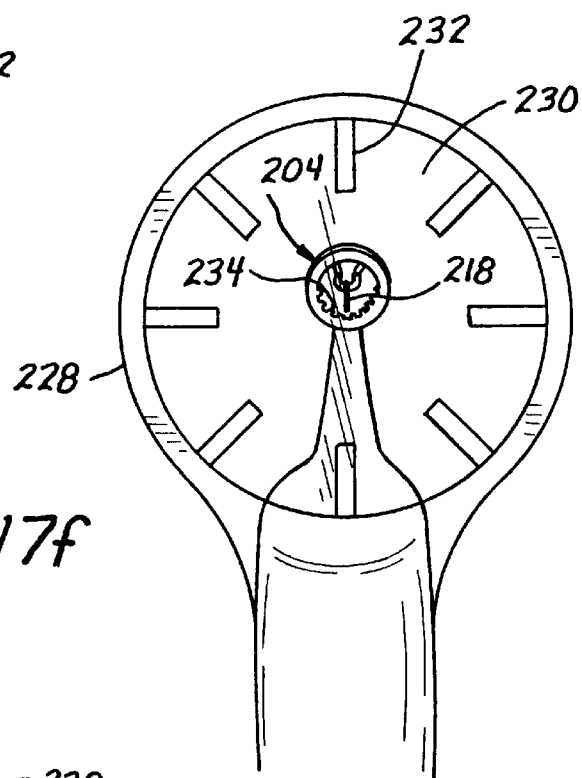
Figure 17D:
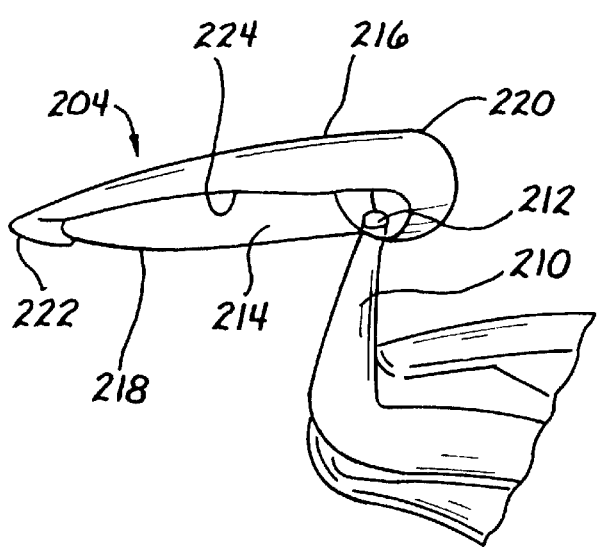

FIGS. 17a–17f illustrate a still further urethra scope 200 having a handle 202, an insertion probe 204, and a viewing lens 206. Again, the handle 202 preferably comprises a pistol grip configuration, such that the insertion probe 204 extends distally from the barrel portion thereof and the viewing lens 206 is in the location of the pistol sight. FIG. 17c is a cross-sectional view showing a curvilinear path 208 within the handle 202 through which a flexible source 210 of illumination may be passed. With reference to FIG. 17d, the flexible light source 210 terminates at a distal tip 212 at the proximal end of the insertion probe 204. In this way, a hollow interior space 214 of the insertion probe 204 is illuminated. The inner walls of the insertion probe 204 may be reflective or, alternatively, transparent.

As best seen in FIG. 17d, the insertion probe 204 comprises a partially tubular upper wall 216 and at least one tissue spreading strut 218. The upper wall 216 extends from a generally annular proximal end 220 to a tapered distal tip 222, and inbetween, a visibility window is created by the side edges 224 of the upper wall 216. The at least one strut 218 extends from the proximal end 220 to the distal tip 222 across the visibility window. The circumferential extent of the upper wall 216 is relatively narrow such that the opposing side edges 224 define an arc therebetween that is desirably less than 50 percent of a tube, and more perfectly less than 30 percent of a tube.

FIGS. 17e and 17f best illustrate the relationship between the lens 206 and the insertion probe 204. The lens 206 comprises an annular bracket 228 within which a circular optical portion 230 is mounted. The optical portion 230 includes a plurality of radially oriented slots 232 evenly distributed around its periphery and extending, for example, inwardly approximately half or a third of the radius of the optical portion. As with other embodiments, the lens 206 is aligned with the longitudinal axis of the insertion probe 204. The proximal end 220 of the insertion probe 204 comprises a partially crenelated inner edge 234 formed by a series of alternating teeth and grooves. In modified embodiments, either or both of the radially oriented slots 232 and partially crenelated inner edge 234 may be moved, modified or omitted.

In operation, a surgeon passes a needle through one of the radially oriented slots 232 and poises it in one of the grooves of the crenelated inner edge 234 while visualizing the interior space 214 of the insertion probe 204 through the circular optical portion 230. With the insertion probe 204 positioned within the urethra, the surgeon can visualize and access an elongated tunnel of prolapsed tissue within the probe by virtue of the visibility window. In accordance with one aspect of the present invention, the posts of the insertion probes of the present invention are preferably configured and spaced to maintain a lumen within the insertion probe while, at the same time, providing for ample prolapse of tissue into the lumen for facilitating injection of bulking agent into the prolapsed tissue. As shown in, for example, FIG. 13, the insertion probe and posts thereof are preferably constructed to allow each prolapse of tissue to extend at least 10 percent into the lumen of the insertion probe and, preferably 20 percent, and more preferably 30 percent. In modified embodiments, the insertion probe may facilitate prolapses of tissue to even greater extents into the lumen. In the embodiment of FIG. 17, the interaction between the upper wall 216 and the at least one strut 218 spreads the tissue within the urethra apart, and the elongated generally cylindrical space 214 provides the tunnel or lumen. The light source 210 provides illumination, such that the surgeon can inject a bulking agent into the tissue of the urethra partially or all of the way along the length of the probe 204.

Figures 18A, 18B:
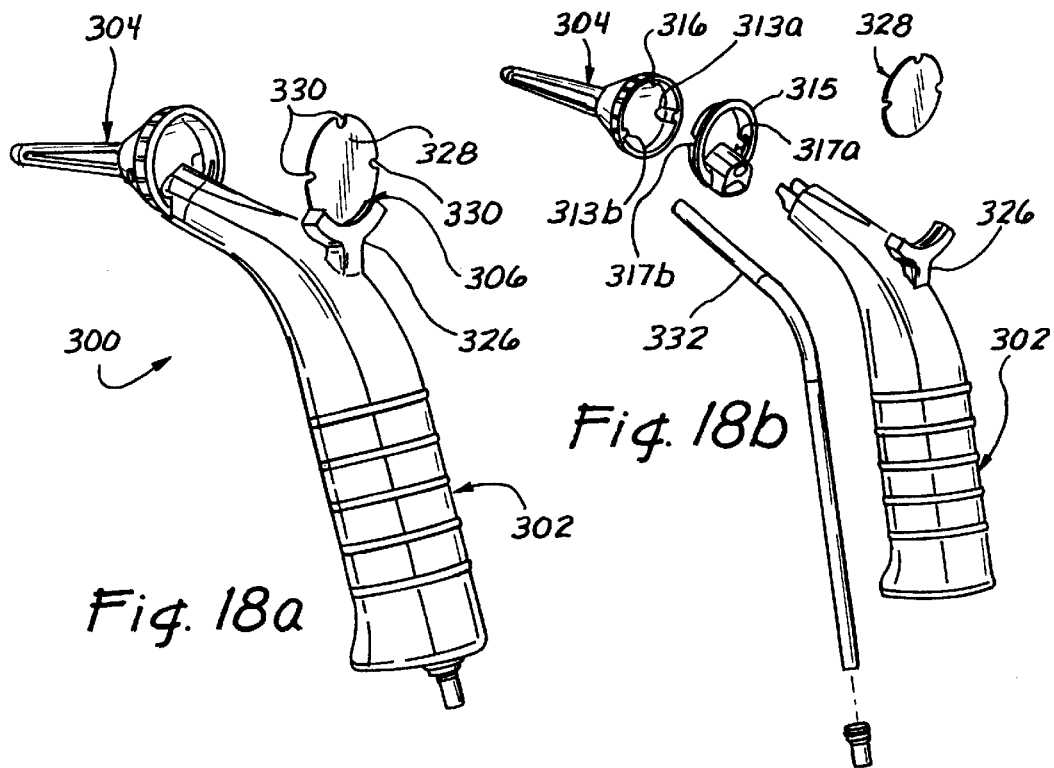
FIGS. 18a–18d are assembled and exploded views of a still further urethra scope of the present invention.
Figures 18C, 18D:
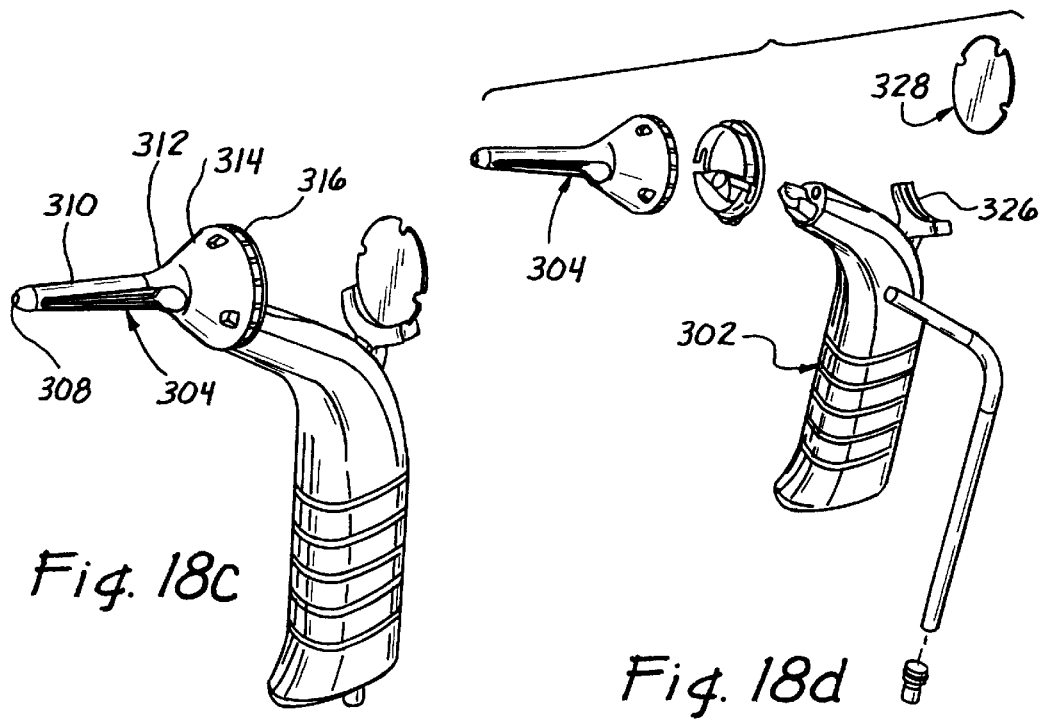

FIGS. 18a–18d and 19a–19d illustrate another urethra scope 300 of the present invention that has a handle 302, an insertion probe 304, and a lens assembly 306 mounted on the handle. The probe 300 is in many ways similar to the probe 100 shown in FIG. 14, except for the shape of the insertion probe 304 and lens assembly 306. With particular reference to FIG. 18c, the insertion probe 304 includes an open distal tip 308, a generally tubular but gradually tapering insertion length 310, a curvilinearly flared first expansion portion 312, a generally conical second expansion portion 314, and a proximal ring 316 having a plurality of ribs there around. As described previously, the insertion probe 304 is hollow such that an interior space or lumen is created for passage of, for example, a surgical needle.

With reference to FIG. 19a, the insertion probe 304 includes a pair of opposed elongated visibility windows 320 extending substantially along parts of the insertion length 310 and the first expanding portion 312. The circumferential extent of each window 320 preferably increases from the distal end to the proximal end, generally in conformance with the increasing diameter of the insertion probe 304. As seen in FIG. 19b, a third visibility window 322 is preferably provided on the underside of the insertion probe 204. As can be seen, for example, in FIG. 19d, this window similarly extends the same length as the other two windows 320 as presently preferred and preferably has generally the same gradually widening configuration from the distal end to the proximal end.

In contrast to the lens mounting bracket 108 of FIG. 14, and as seen, for example, in FIG. 18a, the lens assembly 306 includes a truncated lens mounting bracket 326 and further includes a generally circular optical portion 328. Three notches 330 are provided around the periphery of the optical portion 328 at the twelve o'clock, three o'clock, and nine o'clock positions. The notches 330, which may be greater or fewer in number and location, enable surgeons to rest injection needles therein during operation of the urethra scope 300.

As can be seen in FIG. 18b, the insertion probe 304 preferably comprises at least one notch and, more preferably, two notches or platforms 313a and 313b formed on the inner surface of the insertion probe 304 and, more preferably, formed on the inner surface of the proximal ring 316. More than two notches can be used in modified embodiments. The two notches 313a and 313b operate similarly to the notches 113a and 113b of FIG. 16c, for example, by aiding in the placement of, for example, an injection needle, and may comprise alternative forms and locations within the insertion probe 304 in modified embodiments so long as they provide a function of needle stabilization. In the illustrated embodiment, the two notches 313a and 313b further operate to secure the insertion probe 304 to a bayonet disk 315 via slots 317a and 317b.

In operation, the insertion probe 304 is positioned within the urethra with the open distal tip 308 closely adjacent to the sphincter muscle. This positioning can be facilitated by the act of a surgeon visualizing the sphincter muscle through, for example, the open distal tip 308. The soft tissue of the urethra tends to prolapse through the visibility windows 320, 322 and into the hollow interior space of the insertion probe 304. Preferably with the aid of illumination, as provided by a light source 332 (FIG. 18b), the surgeon can inject a bulking agent into the soft tissue that has prolapsed through the visibility windows 320, 322. Specifically, the injection needle can be positioned in one of the notches 330 and passed through the proximal ring 316 into the insertion probe 304. The three notches 330 enable injection of the bulking agent at the three o'clock, six o'clock, and nine o'clock positions.

A urethra scope 400 having a disposable insertion probe and lens assembly 402 is illustrated FIGS. 20–22. The urethra scope 400 is in many ways similar to the urethra scope 300 of FIGS. 18a–18d and 19a–19d, with the exception of a detachable insertion probe and lens assembly 402 as best seen in the exploded views of FIGS. 20b and 20c, and the isolation view of FIG. 22. The urethra scope 400 includes a pistol-type handle 406 that receives a flexible light source 408 therethrough. The detachable insertion probe and lens assembly 402 comprises an insertion probe 410, the configuration of which in the illustrated embodiment is similar to that of the insertion probe 304 of FIGS. 18a–18d and 19a–19d. Moreover, the detachable insertion probe and lens assembly 402 comprises a lens 414, the configuration of which in the illustrated embodiment is similar to that of the optical portion 328 of FIGS. 18a 18d and 19a–1 9d. In modified embodiments, either or both of the insertion probe 410 and the lens 414 may comprise any of the similar or analogous constructions discussed herein, so long as they are joined together to form a detachable insertion probe and lens assembly.

Figure 20B:
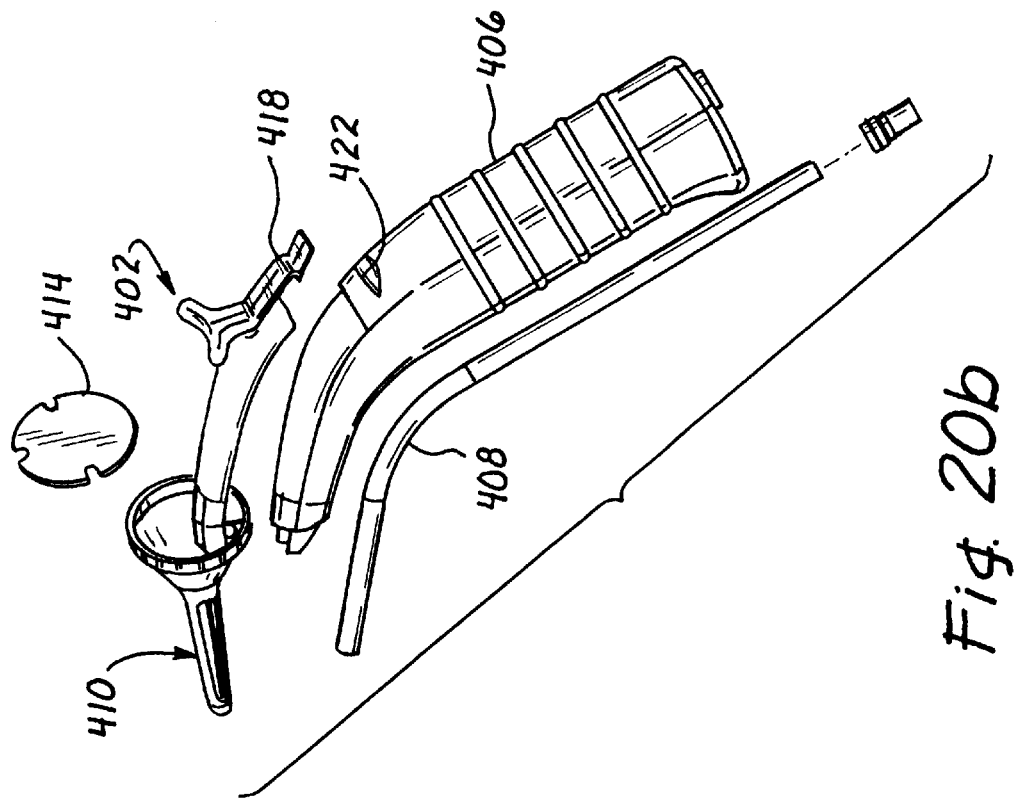
FIGS. 20a–20d are assembled and exploded perspective views of a still further urethra scope of the present invention having an insertion probe and lens mount formed as a removable unit.
Figure 20A:
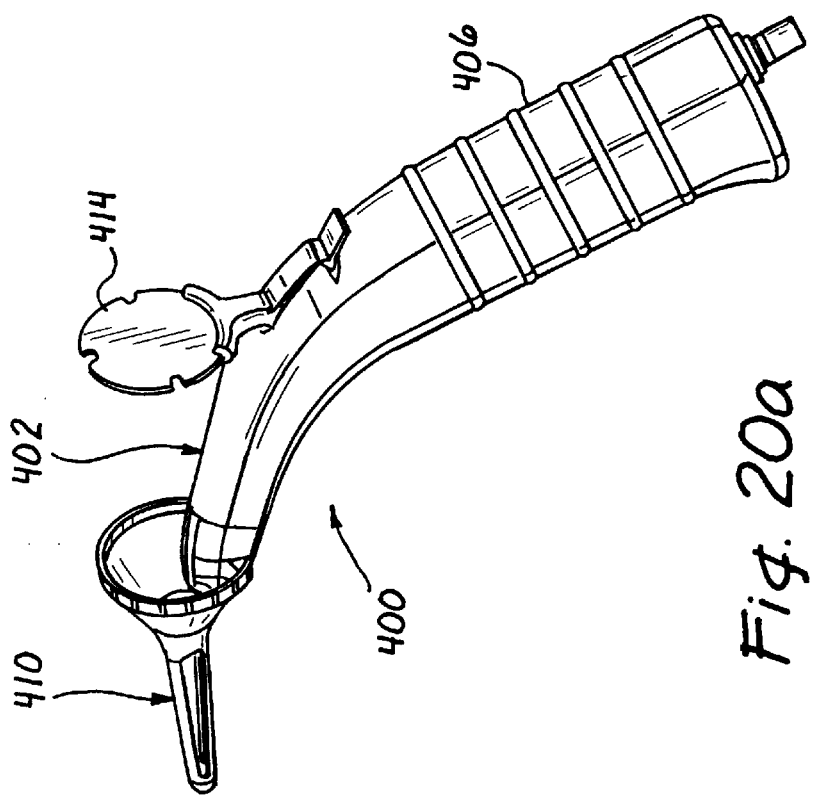
Figure 20D:
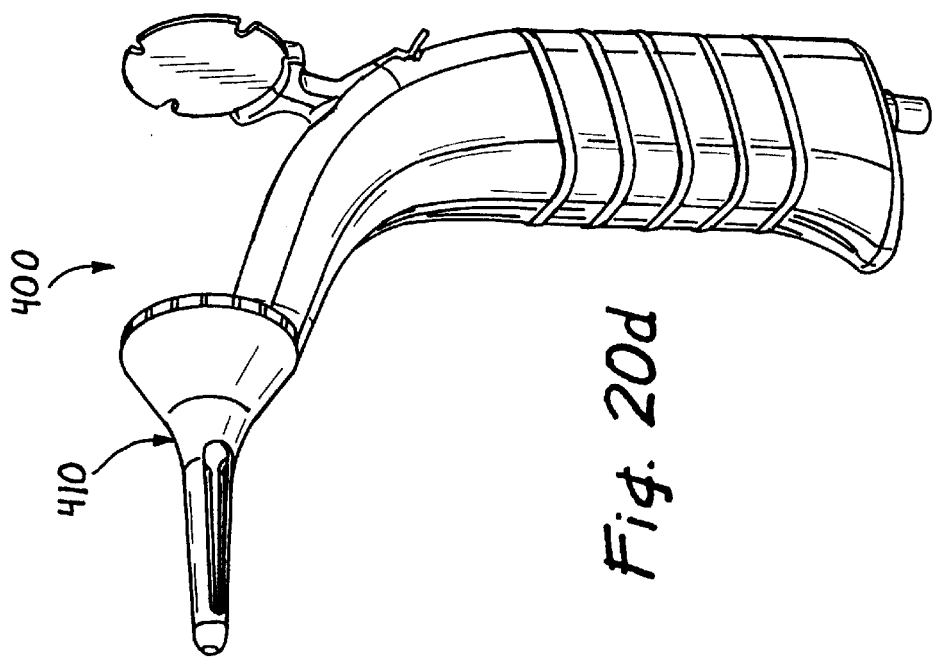
Figure 20C:
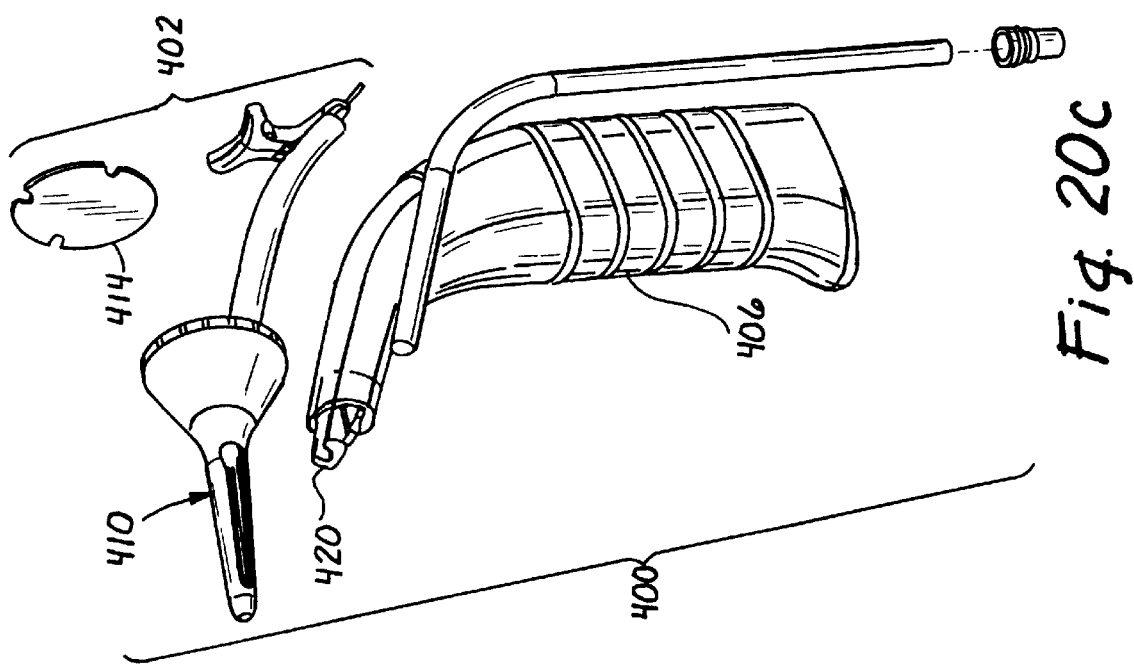

As can be seen in FIG. 22, the detachable insertion probe and lens assembly 402 includes the aforementioned insertion probe 410 and lens 414, a lens mounting bracket 412, a connecting strut 416 extending between the insertion probe 410 and the lens mounting bracket 412, and a latch 418 that removably secures the detachable insertion probe and lens assembly 402 to the handle 406. The distal tip of the handle 406, as best seen in FIG. 20c, terminates in a light source platform 420 that engages an inner feature of the insertion probe 410, as shown, for example, in FIG. 22. The latch 418 cams over and engages a locking notch 422 (FIG. 20b) in the handle. In this way, the detachable insertion probe and lens assembly 462 can easily and instantly be coupled and decoupled from the handle 406 for sterilization and/or disposal. In modified embodiments, the detachable insertion probe and lens assembly 402 may be secured to the handle 406 using other means. For example, the locking notch 422 may instead comprise a slot, the latch 418 may instead comprise a tongue, and a clamp, notch, cam, latch or other mechanical securing mechanism may be used to secure the distal end of the detachable insertion probe and lens assembly 402 to the distal end of the handle 406. In operation, for example, in accordance with one of the modified embodiments, the proximal end of the detachable insertion probe and lens assembly 402 is first secured to the handle 406 and, subsequently, the distal end of the detachable insertion probe and lens assembly 402 is secured to the distal end of the handle 406. Additional securing mechanisms, including screws, hook-and-loop fabric fasteners, longitudinal slots and ribs wherein the distal end of the detachable insertion probe and lens assembly 402 is slid longitudinally or transversely and/or snap fitted to the handle 406, lever action types of securing, pin and hole snap fits, etc, may be incorporated to instantly, conveniently and removably secure the distal end of the detachable insertion probe and lens assembly 402 to the distal end of the handle 406 for instant removal. Each of the above securing features is included within the scope of the present invention, to facilitate instant assembly and removal of the detachable insertion probe and lens assembly 402. In addition, all combinations of the presently disclosed assembly/removal features of this paragraph which are not mutually inconsistent or incompatible are also included within the scope of the present invention for facilitating instant assembly and removal of at least one of the proximal, distal and intermediate portions of the detachable insertion probe and lens assembly 402.

Figure 23:
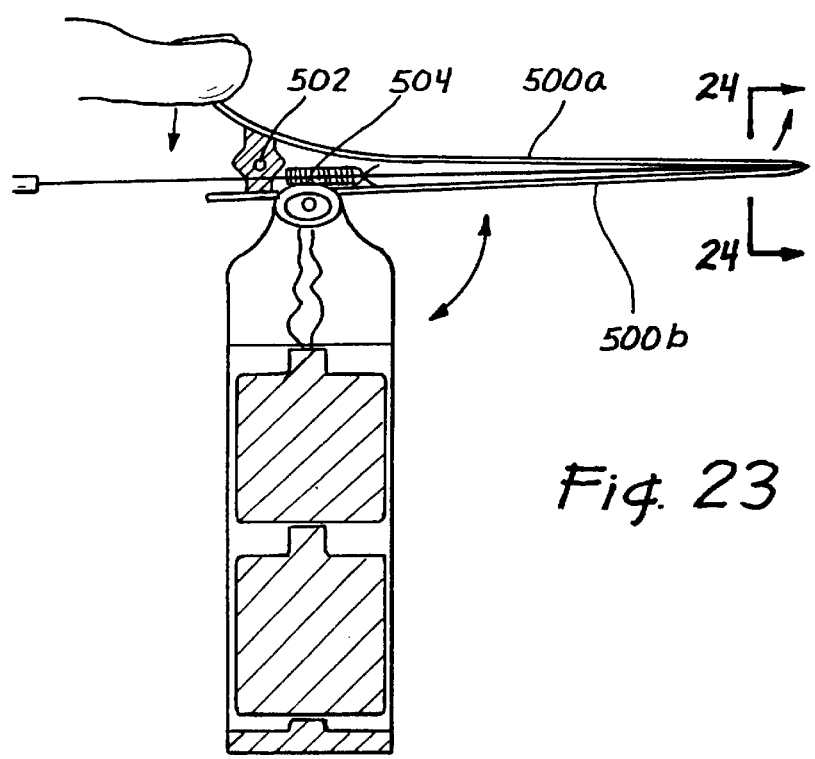
FIG. 23 is a partial sectional side elevation view of a still further urethra scope of the present invention having an insertion probe with movable blades.
Figure 25:
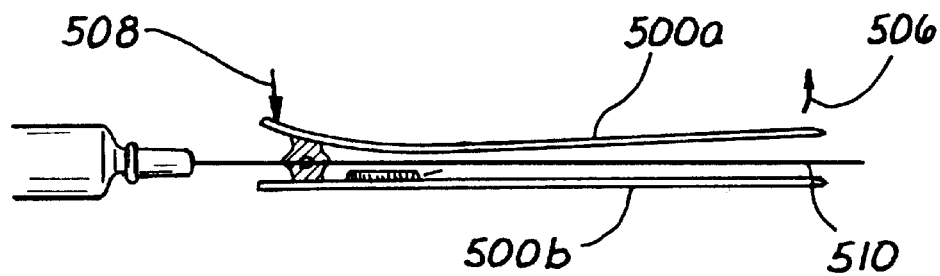
FIG. 25 is a side elevation view of just the insertion probe of FIG. 23 with its blades open and showing the interaction of a tissue-bulking syringe therewith.

Turning to FIGS. 23 and 25, an alternative urethra scope of the present invention comprises two blades 500a and 500b, each of which is preferably about 10–15 cm long. The two blades 500a and 500b are connected to each other through a joint spring mechanism 502 and are designed to be easily inserted into the female urethra with smooth, round edges (similar to a speculum used in gynecology to examine the female vagina). The female urethra is 2.5 to 4 cm long and can be expanded to at least 7–8 mm in diameter. Each of the two blades can be, for example, approximately 2 mm thick, and the diameter of the injection needle may be, for example, approximately 2 mm thick. The length of the needle may be, for example, about five to seven inches, which may be substantially shorter than prior art needles for injecting urinary bulking agents. The shorter needle can allow for a much lower insertion force of the bulking agent therethrough (due to the shorter length) so that bulking agents can be more easily injected into the urethra and/or sphincter muscle tissue. Moreover, a smaller diameter needle may be used due to the smaller insertion force.

A light source 504 for illuminating the channel between the two blades 500a and 500b, may be removable and not disposable. Although an LED or equivalent light source 504 is shown, other illumination means may be incorporated to facilitate direct viewing of the surgical area through the visual passageway provided between the two blades. It is preferred to minimize the obstruction of the joint spring mechanism 502 and the light source 504 to maximize the quality and size of the visual passageway.

Figure 24A:
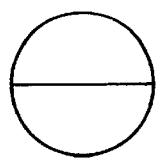
FIGS. 24a–24f are sectional views showing various cross-sectional shapes of the movable blades of the insertion probe of FIG. 23.
Figure 24B:
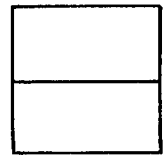
Figure 24C:
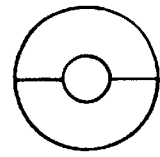
Figure 24D:
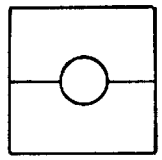
Figure 24E:
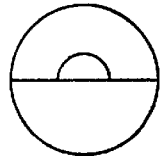
Figure 24F:
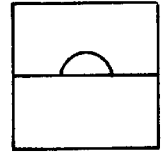

FIGS. 24a–24f illustrate various cross sectional shapes of the two blades 500a and 500b at the distal end of the urethra scope, as viewed along line 24—24 of FIG. 23. In FIG. 24a the two blades have semi-circular cross-sections at or near further tips, and in FIG. 24b the two blades have rectangular cross-sections at or near their tips. FIG. 24c corresponds to the configuration of FIG. 24a, with a center channel formed in the two blades to facilitate advancing and retracting of the needle when the two blades are partially or fully closed such as, for example, within a small urethra or appropriate operating condition where a small diameter of the urethra scope is desired. FIG. 24d corresponds to the configuration of FIG. 24b with a center channel formed therein. The center channels of FIGS. 24e and 24f are formed in only one of the two blades.

In order to reduce the risk of infection and assure sterility of the two blades that are inserted into the urethra, the blades can be covered with sterile, disposable sleeves (not shown) similar to latex condoms. Similarly, the above-discussed conical embodiments of insertion probes may be coated with a similar, preferably transparent, sleeve. The urethra scope itself can be manufactured from surgical stainless steel for better durability and re-use, but may also be manufactured from plastic to reduce costs. In a plastic configuration, for example, the urethra scope may be manufactured to be disposable, so that the needle, spring joint, light source (but not the light source power supply) and blades are all discarded after use.

The visual passageway can provide a very natural and intuitive operating environment for the surgeon, as distinguished from video monitors, which may be expensive and artificial. Moreover, the manual operation of the two blades to, inter alia, increase and decrease the diameter of the tissue passage, e.g., urethra, and to move one of the blades proximally and/or distally relative to the other, can allow the surgeon greater maneuverability, manipulation, access and tactile feedback during the surgical procedure, compared to prior art devices.

As shown in FIG. 25, the blades can be opened (tips moved apart) like a beak in the direction of the arrow 506 by e.g. pressing the thumb on the upper blade's proximal end portion near to the joint, as indicated by arrow 508. This expansion capability enables the physician to create the visual passageway between the two blades, and to maximally expand the urethra from inside. The physician can feel through application of pressure from his or her thumb onto the proximal end of the upper blade, the proper amount of force that should be applied to open the urethra to a comfortable but not excessive diameter. Moreover, the physician can visually inspect the inner wall of the urethra to ensure an optimal opening of the lumen of the urethra. In all embodiments it is preferred that a visual passageway between the two blades is created upon the blades being actuated and separated. In an embodiment wherein the user presses his or her thumb against the proximal end of the upper blade, the visual passageway is preferably illuminated with the light source 504 or an equivalent thereof.

Figure 26:
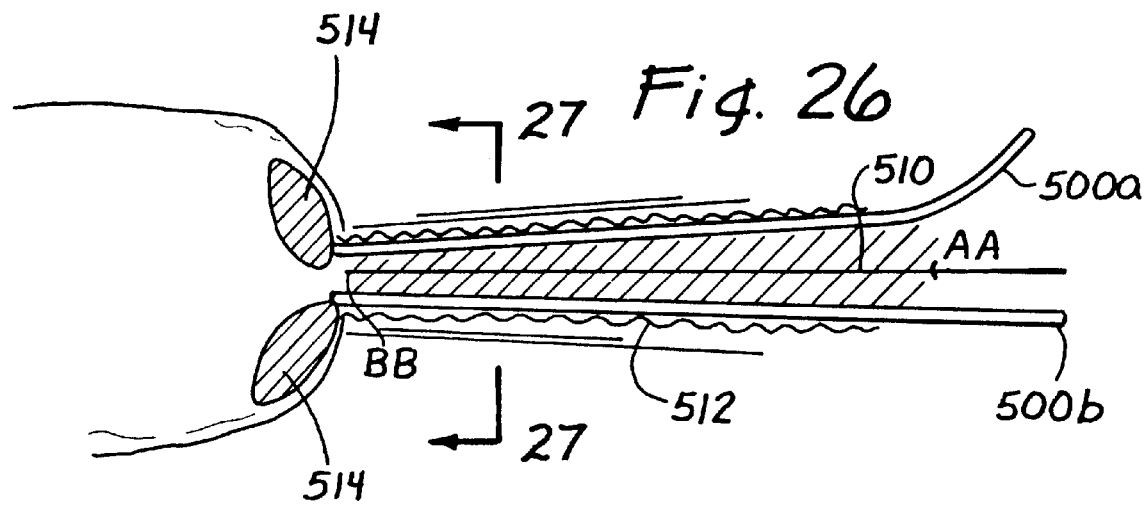
FIG. 26 is a sectional view of the insertion probe of FIG. 23 positioned in the urethra with its blades open.

FIG. 26 illustrates the insertion of the two blades 500a, 500b and needle 510 into a female urethra 512. In the presently preferred embodiment, the needle is retracted and the blades closed during insertion of the urethra scope into the urethra. Although not illustrated, the urethra scope of the present invention may be used in a variety of medical applications, including various surgical procedures within the urethra. With the needle not present or retracted and the blades closed, the urethra scope can be advanced through the urethra and urinary sphincter muscle 514 into the bladder and, subsequently, withdrawn slightly to align, for example, the distal tips of the blades just proximally of the urinary sphincter muscle.

Figure 27:
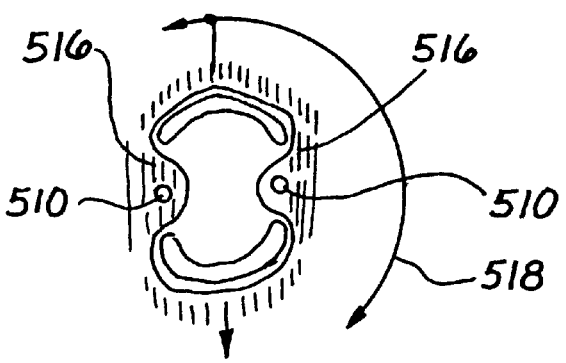
FIG. 27 is a cross-sectional view of the insertion probe as positioned in FIG. 26 taken along line 27—27.

FIG. 27 is a cross-section of the inserted blades 500a, 500b showing the alternate positioning of the needle 510 in sections of tissue 516 that have prolapsed through side openings between the blades into the visual passageway. Arrow 518 indicates the rotatability of the blades 500a, 500b to re-orient the side openings created therebetween.

Once the physician has positioned the urethra scope, he or she can insert the needle through the urethra scope and into the tissue to be treated, for subsequent injection of bulking agent into the tissue. As previously described with respect to FIGS. 12a–12d, for example, bulking agent is first injected into the six o'clock position to form a first mucosa bulge, the ten o'clock position to form a second mucosa bulge, and then into the two o'clock position to form a third mucosa bulge. The user can inspect the mucosa bulges via the visual passageway. Various viewing angles can be formed by changing the orientation of the two blades, including separation distance and relative proximal/distal orientation of the two blades relative to one another. The urethra scope can be advanced up to, within, and beyond (distal) of the three mucosa bulges for tactile and visual inspection.

The urethra scope of the present invention facilitates true tactile testing of the mucosa bulges, via, for example, opening of the passageway between the mucosa bulges, to ensure surgical success. The physician will be able to recognize whether the force applied via his or her thumb to open the passageway (or compress one or more of the mucosa bulges) is too small or too large. If for example one or more of the mucosa bulges are determined by the surgeon to be too large or nondisplaceable, the surgeon can use the blades to massage and redistribute the bulking agent for a more functionally suitable distribution of the bulking agent.

In general, the surgeon can easily move the blades forth and back within the urethra in order to inject specific areas with the urinary bulking agent and to ensure a proper result of the injection procedure (adaptation of the bladder neck and urethral mucosa), through both visual and tactile means, as the urethra scope is, for example, retracted. More particularly, in a presently preferred embodiment, after the three mucosa bulges are formed the urethra scope can be positioned so that the distal tip thereof is just proximal of the area including and/or adjacent to the urinary sphincter, as shown in FIG. 26. As shown in FIG. 27, when the blades are opened the mucosa of the urethra will slightly prolapse into the side slots between the two blades along the length of the urethra (i.e., along the length of the two blades within the urethra). The surgeon can see the full surface of each longitudinally-extending prolapse, and thus the ensuing injection procedure can be performed under the direct vision of the surgeon. Namely, the surgeon can add additional bulking agent into the prolapsed tissue areas as shown in FIG. 27 at, for example three and nine o'clock. The needle can be inserted through the entire section of prolapsed tissue, entering at point AA in FIG. 26 and terminating within the tissue at point BB near the urinary sphincter 514. Bulking agent can then be injected at point BB and, subsequently, at one or all points between point AA and point BB as the needle is withdrawn. The procedure is then repeated for the second of the two prolapsed tissue areas between the two blades. Thus, in one embodiment, two longitudinally-extending enhanced-tissue structures are generated at the three o'clock and nine o'clock positions. Subsequently, the entire urethra scope can be rotated forty-five degrees, for example, and the process repeated to form, for example, two longitudinally-extending enhanced-tissue structures at the twelve o'clock and six o'clock positions.

In modified embodiments of the invention, three or more movable blades may be used, and the number of mucosa bulges may be increased or decreased alone, or in combination with various numbers/configurations/positionings of longitudinally-extending enhanced-tissue structures. In addition to changing or modifying the number of blades, the shape and/or configuration of the blades may be changed. For example, the curvature, dimensions and/or spacing of one or both of the blades can be modified to affect, inter alia, the type of tissue prolapses therebetween. The blades may be configured, for example, so that they open in a parallel fashion instead of pivoting about the joint spring. The configuration of the blades opening in a parallel fashion generates substantially the same spacing therebetween at every point along the two parallel blades. Moreover, the type of biasing element may be modified. For example, the two blades can be reverse-biased, so that pressure must be applied by the surgeon to close the blades. Regardless of the biasing type, one or more ratchet elements or other fixing means may be incorporated into the urethra scope to thereby allow the surgeon to fix and hold a particular spatial distribution between the two blades.

Figure 28A:
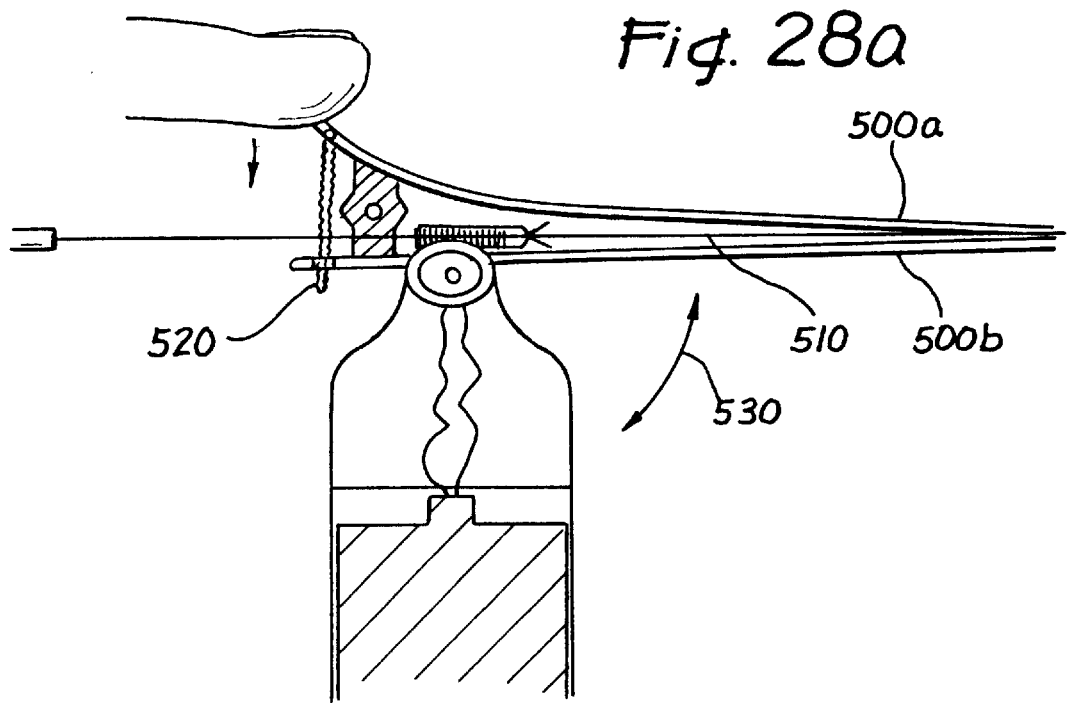
FIGS. 28a and 28b are partial sectional side elevation views of other urethra scope embodiments of the present invention having movable blades and ratcheting locking mechanisms.
Figure 28B:
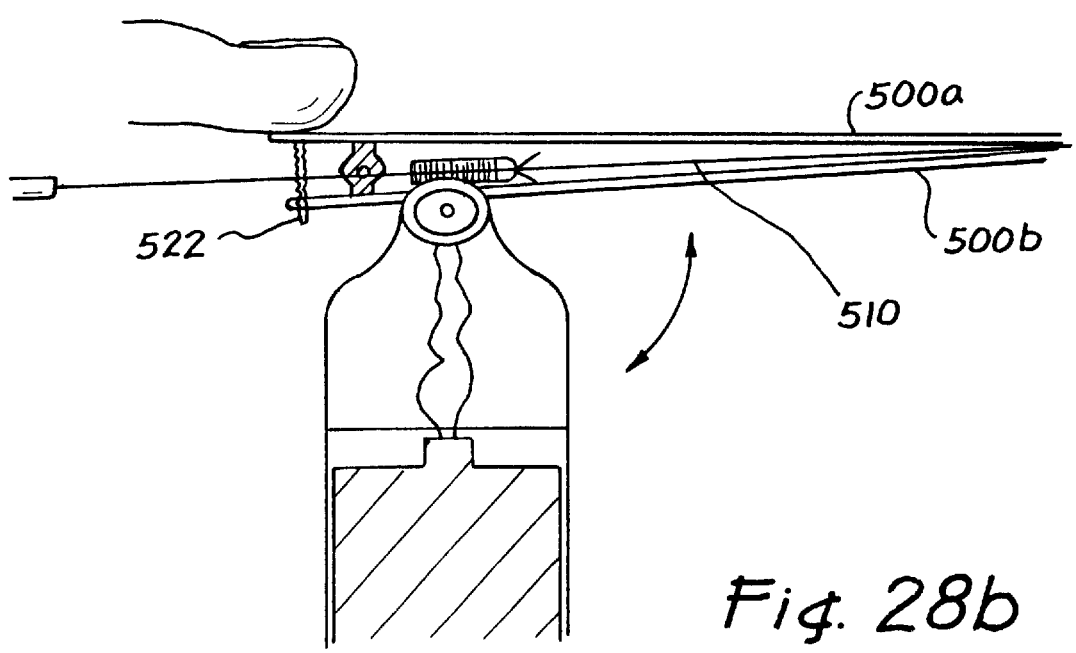

FIGS. 28a and 28b show ratchet-type elements 520, 522 for allowing the user to fix and hold the two blades to a certain open configuration. In addition to ratchets, other mechanical and frictional means may be used to facilitate fixing of the blades in a particular open position during one or more of the surgical procedures, to thereby free the surgeon's hands and facilitate greater stability. In one embodiment, the blades are manufactured in a fixed, non-movable position. In another embodiment, an odoscope is used with a disposable tip for fitting into the urethra of the patient. In order to store the urethra scope more efficiently, the head of the device can be tilted down as indicated at 530 in FIG. 28a, similarly to a laryngoscope used in anesthesia to intubate patients.

The light source for the working canal can be disposed on, slightly recessed in, or entirely recessed within one or both of the two blades, pointing directly or partially toward the distal end of the urethra scope. The light source when fully recessed within one or both of the blades can be configured to point in a direction transverse to the longitudinal axis of the urethra scope, i.e., in a direction across the visual passageway toward the other of the two blades, or the light source can be configured to shine into and along the length of the blade toward the distal end. Any intermediate orientation of the light source could also be adapted. Moreover, more than one light source may be disposed on or in each of the blades at one or more of the above-noted orientations. The light sources may comprise light pipes or fiber optics which connect to external or removable light pipes, fiber optics or light sources. Thus, in a presently preferred embodiment, the light pipes or fiber optics can be detached from the external or removable light pipes, fiber optics or light sources for sterilization or disposal of the urethra scope. In such a configuration where, for example, the urethra scope is disposable, the external or removable light pipes, fiber optics or light sources are removed and only the relatively inexpensive light pipes or fiber optics affixed to or formed within the blade or blades are disposed of with the disposable urethra scope. In a presently preferred embodiment, each of the blades is constructed of a medical grade plastic (e.g., polycarbonate) by injection or compression molding, for example, in order to facilitate light pipe technology wherein the light from one or more LEDs or bulbs is directed through each blade, so that each blade itself serves as a light pipe. The effect is either or both of the blades being illuminated to thereby illuminate the surgical area.

Figure 29A:
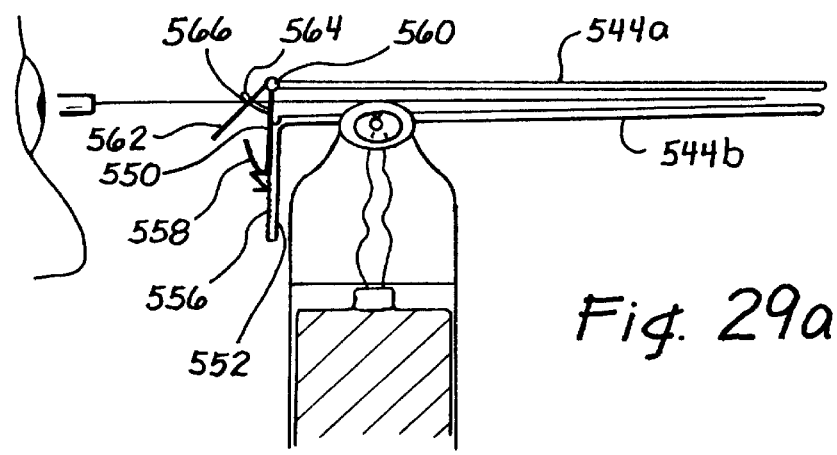
FIGS. 29a–29c are partial sectional side elevation views of urethra scopes having movable blades and alternative mechanisms for moving and securing the blades.

One embodiment incorporates ratchet elements into the urethra scope, to thereby allow the surgeon to fix and hold a particular spatial distribution between the two blades. The mechanism of U.S. Pat. No. 3,176,047 to Moore et al. can be used, and the contents of Moore et al. are incorporated herein by reference. FIG. 29a shows the mechanism of Moore et al. used in the present invention, allowing for both parallel distance and relative angular relationship movement of the two blades. Vertical slide 550 may be moved vertically along depending member 552 which depends from lower blade 554b. The lower end of the depending member 552 is formed with ratchet teeth 556 to allow a pawl 558 to selectively lock the slide 550 in a vertical position as it is moved upwardly. The end of the pawl 558, disposed distally the ratchet teeth 556, may be depressed to allow the pawl to be disengaged from the ratchet teeth, thereby releasing the slide to be movable downwardly. As the slide 550 is moved upwardly, the upper blade 554a moves away from the lower blade 554b while maintaining its angular relationship to the lower blade.

The upper blade 554a is pivotally attached to slide 550 at spring mechanism 560. The spring mechanism is biased to move the ends of blades 554a, 554b, disposed distally of the spring mechanism, together. The upper blade 554a has a depending member 562 forming a hole through which a tongue 564 formed on vertical slide 550 extends. The tongue 564 is biased to press against the lower end of the hole of depending member 562 and has ratchet teeth 566. Depressing depending member 562 causes the end of the upper blade 554a, disposed distally of the spring mechanism 560, to move away from the lower blade 554b and thereby increase the distance between that end and the complementary end of the lower blade. The slide 550, depending member 562, and the tongue 564, are preferably disposed to the side, outside of the user's line of view. In this and other embodiments the mentioned elements should cause the least visual obstruction to the user viewing the urethra between upper and lower blades.

Figure 29B:
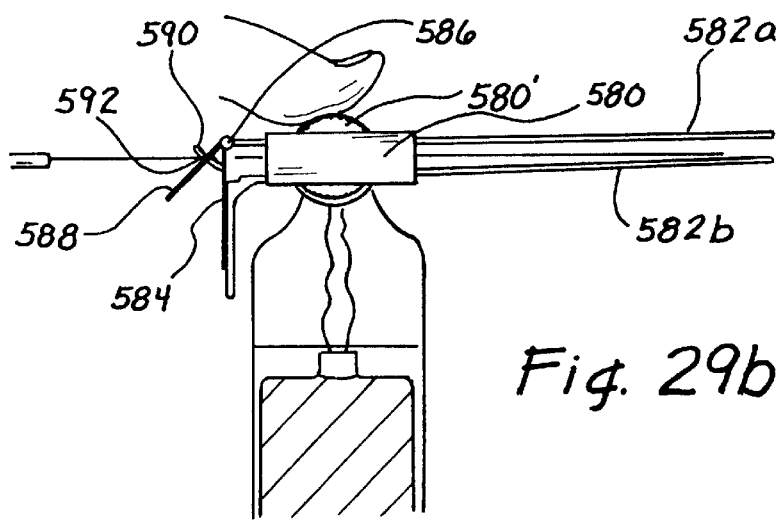

FIG. 29b shows a further modification of the embodiment of FIG. 29a in which a thumbwheel mechanism 580 is used to adjust the relative distance between upper blade 582a and lower blade 582b, while maintaining the relative angle of the two blades. The upper blade 582a is pivotally attached to slide 584 at spring mechanism 586. The spring mechanism 586 is biased to move the ends of blades 582a and 582b, disposed distally of the spring mechanism, together. The upper blade 582a has a depending member 588 forming a hole through which a tongue 590 is formed on vertical slide 584. The tongue 590 is biased to press against the lower end of the hole of depending member 588 and has ratchet teeth 592. Depressing depending member 588 causes the end of the upper blade 582a, which is distal the spring mechanism 586, to move away from the lower blade and thereby increase the distance between that end and the complementary end of the lower blade.

In this embodiment the user adjusts the thumbwheel 580' to cause the thumbwheel mechanism 580 to move the upper blade 582a while maintaining the relative angle of the two blades. It is to be understood that the thumbwheel of this and other embodiments may be operated by any of the user's fingers as well as the thumb. The index finger is shown in FIG. 29b by way of example. In this embodiment the thumbwheel is shown mounted in a vertical orientation, but it may alternatively be mounted in a horizontal orientation, or at an intermediate orientation relative to the thumbwheel mechanism to avoid obstructing the user's view between the blades. The thumbwheel mechanism can be comprised of a number of elements that will be apparent to one of skill in the art. The upper blade is moved in relation to the lower blade in a monotonic relationship, with rotation in a first direction causing the blades to move away relative to each other and rotation in a second, opposite direction causing the blades to move toward each other.

If the thumbwheel is held in position, either by the thumb or by the lack of the requisite force to actuate the mechanism itself, the blades will also be held in position. Note that this embodiment therefore lacks the pawl teeth 556 of the embodiment of FIG. 29a to lock the blades in relative orientation and, moreover, may be formed with or without elements 550, 560, 562, 564 and 566.

The thumbwheel mechanism 580 might also use a ratcheted mechanism such as those commonly used on fishing reels, allowing the thumbwheel to ratchet the blades away from each other with the ratchet mechanism iteratively locking them in position. Such a mechanism 600 is configured in the embodiment of FIG. 29c. The ratcheting mechanism further requires a release button 602 or other switch to release the blades that have been ratcheted apart. Thumbwheel 600' is shown mounted in a horizontal orientation above thumbwheel mechanism 600, being operated by the user's thumb. It is to be understood that the alternate thumbwheel mechanisms, in horizontal, vertical or other orientations, can be used on all of the embodiments shown having, for example, a thumbwheel.

Figure 29C:
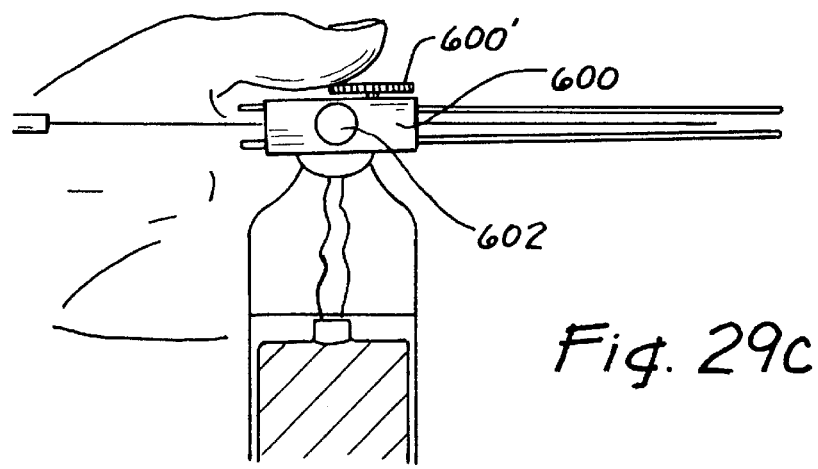

FIG. 29c also shows an embodiment of the urethra scope that lacks a mechanism for changing the relative angular orientation of the upper and lower blades. In this embodiment the blades are constructed in a fixed, substantially-parallel orientation. In this orientation the user adjusts the blades to bring them together, inserts the blades within the urethra, then moves the thumbwheel to cause the thumbwheel mechanism to move the blades apart and thereby dilate the urethra, allowing sufficient room for viewing and insertion of the needle for deposition of bulking material. The lighting for the constructions of FIGS. 29b and 29c is preferably as described in the Moore et al. patent.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

What is claimed is:

1. A surgical device for expanding and viewing tissue, comprising:
   a handle having a proximal end and a distal end, the handle being sized and shaped to be held by a surgeon;
   an insertion probe having a proximal end, an occluded distal end, and a lumen having a longitudinal axis extending between the proximal end and the distal end, the proximal end of the insertion probe being connected to the distal end of the handle and comprising an opening sized to accommodate a needle therethrough and into the lumen; and
   a plurality of windows disposed within the insertion probe, extending along a length of the longitudinal axis and having openings sufficient in size to allow tissue to prolapse therethrough and into the lumen of insertion probe.

2. The surgical device as set forth in claim 1, wherein the handle comprises a lens disposed proximally of the insertion probe.

3. The surgical device as set forth in claim 2, wherein the lens has a diameter which is about equal to a diameter of the opening at the proximal end of the insertion probe.

4. The surgical device as set forth in claim 1, wherein the at least one of the windows extends to the proximal end of the insertion probe.

5. The surgical device as set forth in claim 1, wherein the distal end is occluded with a lens.

6. The surgical device as set forth in claim 1, wherein the at least one of the windows extends at least three quarters of a distance from the proximal end of the probe to the distal end of the probe.

7. The surgical device as set forth in claim 1, wherein the the plurality of windows is a single window extended into two windows by a strut.

8. A device for viewing a urethra and treating urinary stress incontinence, comprising:
   a handle having an attachment constructed to hold a lens;
   an insertion probe connected to the handle and having a proximal end, a distal elongated tip sized to fit within the urethra, and a lumen extending through the insertion probe from the proximal end to the distal elongated tip, the insertion probe including a plurality of viewing windows disposed distally of the proximal end and extending longitudinally along at least a portion of the distal elongated tip to facilitate visualization of a longitudinal portion of the urethra through the lumen; and
   an opening at the proximal end of the insertion probe, the opening being sized to facilitate insertion of a needle through the opening and out one of the viewing windows of the insertion probe.

9. The device as set forth in claim 8, wherein the insertion probe further includes a widened neck portion proximal to the distal elongated tip and the lumen increases in cross-sectional area in the widened neck portion.

10. The device as set forth in claim 9, wherein the distal elongated tip is generally tubular and the widened neck portion comprises a curvilinear flare.

11. The device as set forth in claim 8, wherein the viewing windows are formed on at least one side of the distal elongated tip.

12. The device as set forth in claim 8, wherein the distal elongated tip comprises a generally tubular shape and an elongate section of one side of the tubular shape is removed to form an open area, the distal elongated tip further including a pair of spaced apart struts extending a length of the elongate section in the open area to thereby define the plurality of viewing windows.

13. The device as set forth in claim 8, wherein:
   the viewing windows comprise a first viewing window; and
   a second viewing window extending longitudinally along at least a portion of the distal elongated tip for visualizing a longitudinal portion of the urethra through the lumen.

14. The device as set forth in claim 13, wherein the viewing windows further comprises a third viewing window extending longitudinally along at least a portion of the distal elongated tip for visualizing a longitudinal portion of the urethra through the lumen.

15. The device as set forth in claim 8, wherein the attachment is constructed to hold a lens proximally of the insertion probe.

16. The device as set forth in claim 8, wherein the attachment comprises a lens having a diameter which is about equal in size to a diameter of the proximal end of the insertion probe.

17. The device as set forth in claim 8, wherein the viewing windows extend to the proximal end of the insertion probe.

18. The device as set forth in claim 8, wherein the plurality of viewing windows is a single window separated into two windows by at least one strut.

19. The device as set forth in claim 8, wherein a distal end of the distal elongated tip of the insertion probe is occluded with a lens.

20. The device as set forth in claim 8, wherein:

the insertion probe further includes a widened neck portion proximal to the distal elongated tip and the lumen increases in cross-sectional area in the widened neck portion;

the distal elongated tip is generally tubular and the widened neck portion comprises a curvilinear flare; and a surface of the widened neck portion extends radially outwardly at a steeper angle than a surface of the distal elongated tip.

21. The device as set forth in claim 8, wherein:

the distal elongated tip is generally tubular and an elongate section of one side of the tube is removed to thereby form the viewing windows, the distal elongated tip further including a pair of spaced apart struts extending a length of the elongate section in the viewing windows;

the distal elongated tip comprises a proximal curvilinearly flared portion and a distal substantially conical portion; and the elongate section extends into both the proximal curvilinearly flared portion and the distal substantially conical portion.

22. A surgical device for expanding and viewing tissue, comprising: a handle having a proximal end and a distal end, the handle being sized and shaped to be held by a surgeon; an insertion probe having a proximal end, a distal end occluded with a first lens, and a lumen having a longitudinal axis extending between the proximal end and the distal end, the proximal end of the insertion probe being connected to the distal end of the handle and comprising an opening sized to accommodate a needle therethrough and into the lumen; and at least one window disposed within the insertion probe, the at least one window extending along a length of the longitudinal axis and having an opening sufficient in size to allow tissue to prolapse through the window and into the lumen of insertion probe.

23. The surgical device as set forth in claim 22, wherein the handle comprises a second lens disposed proximally of the insertion probe.

24. The surgical device as set forth in claim 23, wherein the second lens has a diameter which is about equal to a diameter of the opening at the proximal end of the insertion probe.

25. The surgical device as set forth in claim 22, wherein the at least one window extends to the proximal end of the insertion probe.

26. The surgical device as set forth in claim 22, wherein the at least one window extends at least three quarters of a distance from the proximal end of the probe to the distal end of the probe.

27. The surgical device as set forth in claim 22, wherein the window is separated by at least one strut to form a plurality of windows.

* * * * *